(12) United States Patent
Tatum et al.

(10) Patent No.: US 8,540,617 B2
(45) Date of Patent: Sep. 24, 2013

(54) EXTRACORPOREAL PUMPING METHODS

(75) Inventors: Tani Tatum, Bishop, CA (US); Stephen Walker, Franklin, TN (US); Robert W Wilson, Bishop, CA (US)

(73) Assignee: Medical Engineering Company, LLC, Bishop, CA (US)

( * ) Notice: Subject to any disclaimer, the term of this patent is extended or adjusted under 35 U.S.C. 154(b) by 0 days.

(21) Appl. No.: 13/468,972

(22) Filed: May 10, 2012

(65) Prior Publication Data

US 2012/0245405 A1    Sep. 27, 2012

Related U.S. Application Data

(63) Continuation-in-part of application No. 12/806,918, filed on Aug. 23, 2010, now Pat. No. 8,425,396, which is a continuation-in-part of application No. 11/788,585, filed on Apr. 20, 2007, now Pat. No. 7,785,247.

(60) Provisional application No. 61/518,711, filed on May 10, 2011.

(51) Int. Cl.
*A61H 31/00* (2006.01)
*A61M 1/10* (2006.01)

(52) U.S. Cl.
USPC .................................................. 600/16

(58) Field of Classification Search
USPC ...................... 422/44–45; 604/4.01
See application file for complete search history.

(56) References Cited

U.S. PATENT DOCUMENTS

| 3,814,547 | A | 6/1974 | Kitrilakis et al. |
|---|---|---|---|
| 4,360,324 | A | 11/1982 | Ohara et al. |
| 4,369,530 | A | 1/1983 | Robinson et al. |
| 5,044,901 | A | 9/1991 | Fumero et al. |
| 5,171,207 | A | 12/1992 | Whalen |
| 5,360,445 | A | 11/1994 | Goldowsky |
| 5,820,579 | A | 10/1998 | Potkin |
| 6,607,368 | B1 | 8/2003 | Ross et al. |
| 7,189,352 | B2 | 3/2007 | Carpenter et al. |
| 2005/0234287 | A1 | 10/2005 | Weatherbee |
| 2008/0064917 | A1 | 3/2008 | Bar et al. |

OTHER PUBLICATIONS

US Patent and Trademark Office, Non-Final Office Action for U.S. Appl. No. 11/788,585 dated Oct. 26, 2009.

*Primary Examiner* — Carl H Layno
*Assistant Examiner* — Paula J Stice
(74) *Attorney, Agent, or Firm* — Parsons Behle & Latimer

(57) ABSTRACT

An extracorporeal pumping method includes receiving an inlet fluid into a compressible-expandable bladder sealably mounted within a housing and moving an actuating member mounted within a fluid chamber of a hydraulic actuating sub-assembly. A pressure transmissive fluid is displaced from the fluid chamber into the housing. The method includes compressing a volume of the bladder in the housing using the transmissive fluid displaced into the housing, the compressed bladder ejecting the inlet fluid from the bladder to provide an outlet fluid under pulsatile pressure. The actuating member is moved within the fluid chamber and the displaced transmissive fluid is returned from the housing into the fluid chamber. The method includes expanding the compressed bladder in the housing and receiving additional inlet fluid into the bladder. The movement of the actuating member is controlled such that the outlet fluid exhibits a predetermined pulse rate, stroke volume, and upstroke rise time.

20 Claims, 19 Drawing Sheets

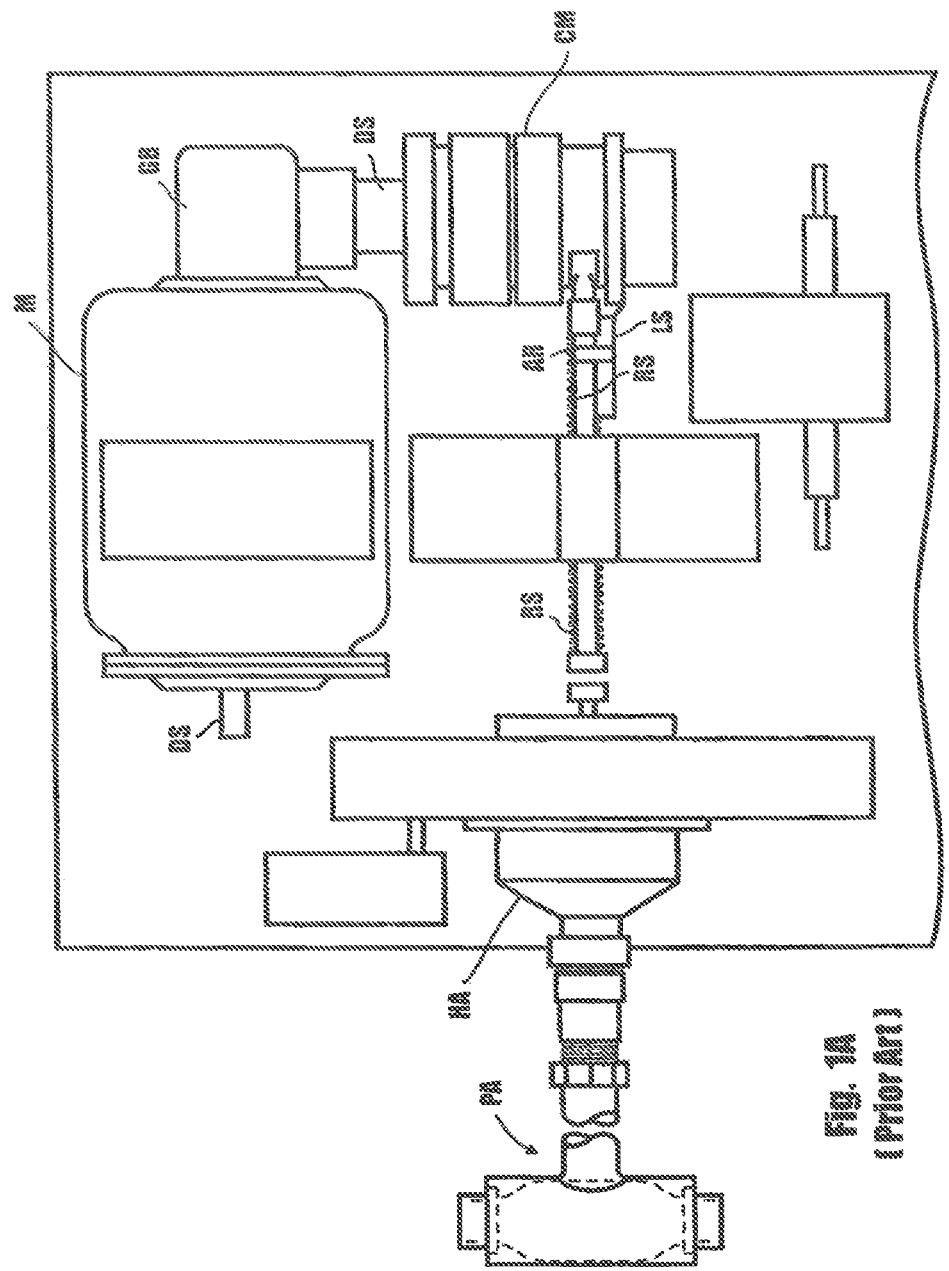

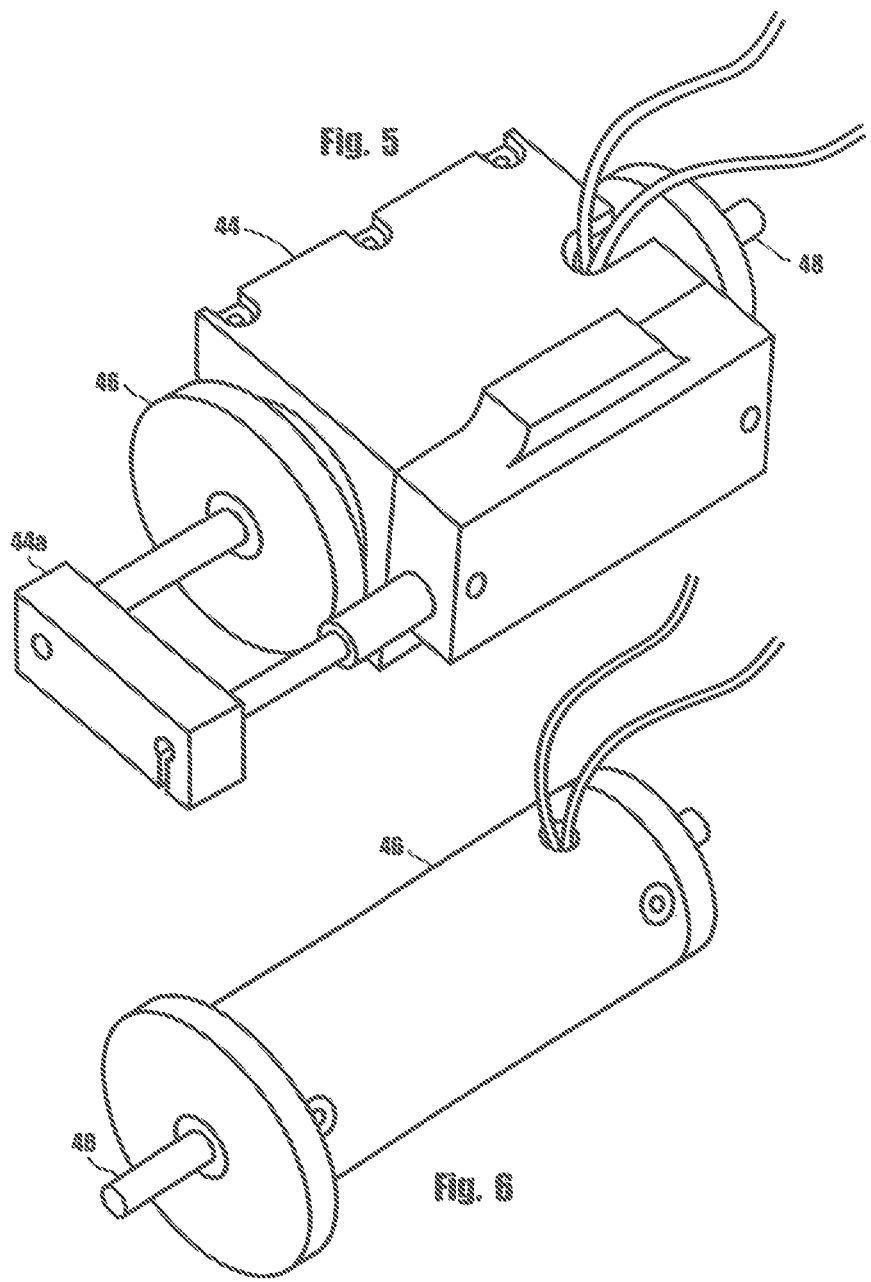

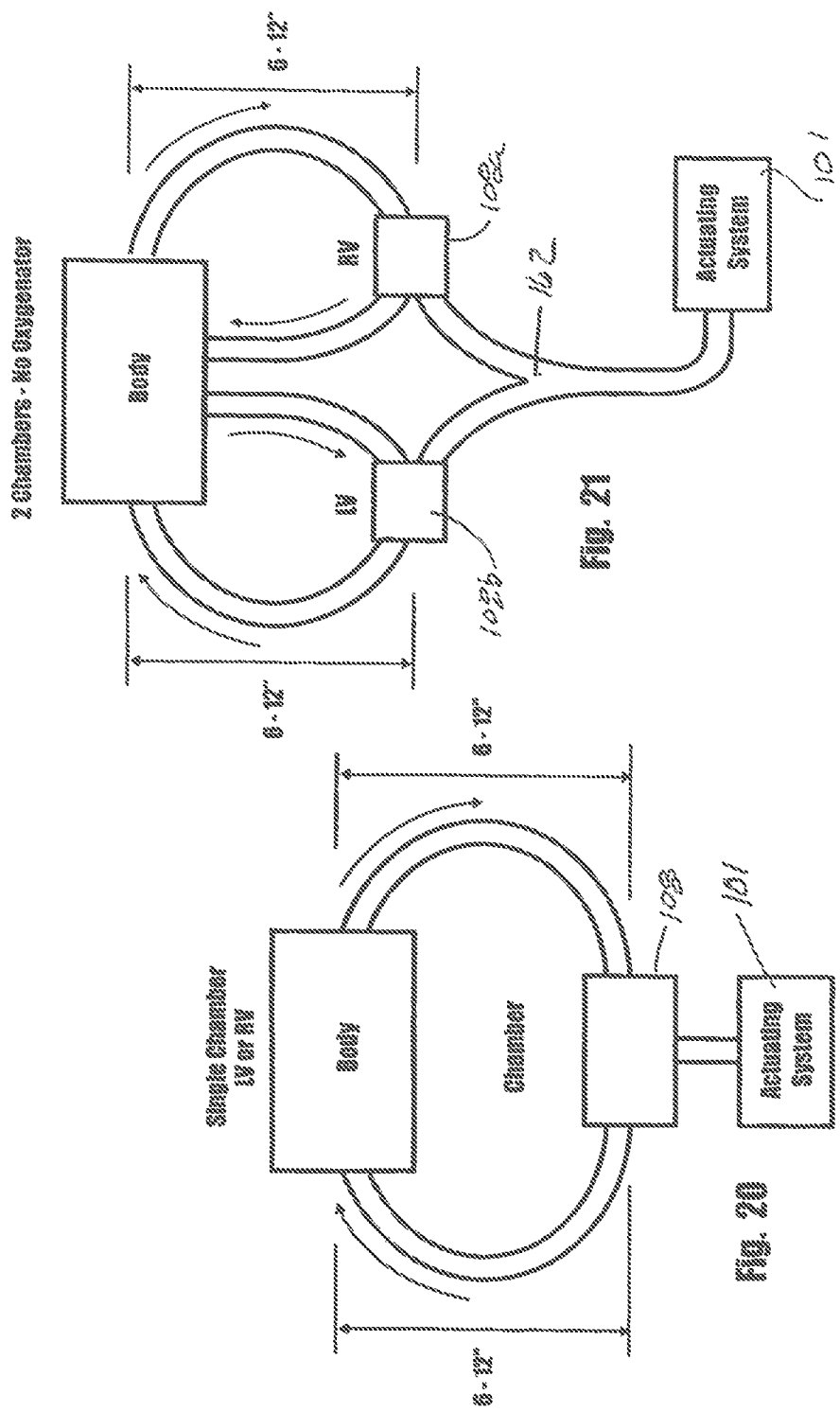

EXTRACORPOREAL PUMPING METHODS

RELATED APPLICATION DATA

The present application claims the benefit of priority under 35 U.S.C. §119 to U.S. Provisional App. No. 61/518,711, incorporated herein by reference, filed May 10, 2011, entitled "Employment of Accurate Physiologic Hemodynamic Emulation of Natural Circulatory Blood Pressure and Flow Patterns". Also, the present application is a continuation-in-part of U.S. application Ser. No. 12/806,918, incorporated herein by reference, filed Aug. 23, 2010 now U.S. Pat. No. 8,425,396, which is a continuation-in-part of U.S. application Ser. No. 11/788,585, incorporated herein by reference, filed Apr. 20, 2007, now U.S. Pat. No. 7,785,247.

TECHNICAL FIELD

The embodiments relate to accurate physiologic hemodynamic emulation of natural circulatory blood pressure and flow patterns for providing extracorporeal circulation in extraction of umbilical cord blood and placenta stem cells, regional stem cell therapy including tissue and organ grafting, cardiopulmonary bypass, ventricular assist, extracorporeal membrane oxygenation (ECMO), organ preservation, fetal cardiac bypass, and regional cancer treatment.

As used herein, the term "physiologic" is defined as something that is normal, neither due to anything pathologic nor significant in terms of causing illness.

BACKGROUND

The importance of inducing extracorporeal circulation that is as physiologic as possible has long been recognized. A pulsatile pump system was conceived in the mid-1950s by heart surgeon Selwyn Roy McCabe. Dr. McCabe worked on a tricuspid valve, which evolved to a 2-chamber pulsatile pump with a number of unique features. The doctor envisioned that such a system could allow quality time for corrective surgery and, ultimately, could prolong life support. Dr. McCabe, who was also trained in internal cardiology and physiology, felt that accurate duplication of blood pressure and flow patterns could have significant advantages to both the major vital organs and to the microcirculation.

The life support system conceived by Dr. McCabe was successfully tested on an adult dog in Bethesda, Md. in early 1957. A neonatal/infant model, the Pediatric Pulsatile Pump, was developed in the early 1970's and a number were sold for research purposes with very successful results.

No accepted method exists for quantifying "pulsatile flow" with respect to extracorporeal pumps. Many systems claiming "pulsatile flow" exhibit physical parameters that are, at best, of indifferent efficacy and, at worst, harmful. Accordingly, it may be possible to improve hemodynamic emulation of natural circulatory blood pressure and flow patterns.

SUMMARY

An extracorporeal pumping method includes receiving an inlet fluid into a compressible-expandable bladder sealably mounted within a housing and moving an actuating member mounted within a fluid chamber of a hydraulic actuating sub-assembly. The fluid chamber contains a pressure transmissive fluid. Transmissive fluid is displaced from the fluid chamber into the housing. The method includes compressing a volume of the bladder in the housing the transmissive fluid displaced into the housing, the compressed bladder ejecting the inlet fluid from the bladder to provide an outlet fluid under pulsatile pressure. The actuating member is moved within the fluid chamber and the displaced transmissive fluid is returned from the housing into the fluid chamber. The method includes expanding the compressed bladder in the housing and receiving additional inlet fluid into the bladder. The movement of the actuating member is controlled such that the outlet fluid exhibits a predetermined pulse rate, stroke volume, and upstroke rise time.

The method may include introducing the outlet fluid into a blood vessel and thereby pumping blood through the blood vessel under the pulsatile pressure. Also, the method may include using the outlet fluid under the pulsatile pressure to extract umbilical cord blood and/or placenta stem cells or to provide stem cell therapy, cardiopulmonary bypass, ventricular assist, extracorporeal membrane oxygenation, organ preservation, fetal cardiac bypass, or cancer treatment.

BRIEF DESCRIPTION OF THE DRAWINGS

Some embodiments are described below with reference to the following accompanying drawings.

FIG. 1A is a partial, top plan view of a portion of the prior art pulsatile pump apparatus developed by Dr. McCabe.

FIG. 5 is a generally perspective view of a voice-coil actuator sub-assembly of the apparatus shown in FIG. 2.

FIG. 6 is a generally perspective view of a voice-coil motor of the assembly shown in FIG. 5.

FIG. 20 is a generally diagrammatic view illustrating a manner of interconnection of the hydraulic actuator sub-assembly and one embodiment of the pulsatile pump sub-assembly with the patient.

FIG. 21 is a generally diagrammatic view illustrating the manner of interconnection of the hydraulic actuator sub-assembly and another embodiment of the pulsatile pump sub-assembly with the patient.

DETAILED DESCRIPTION

Figure 1:
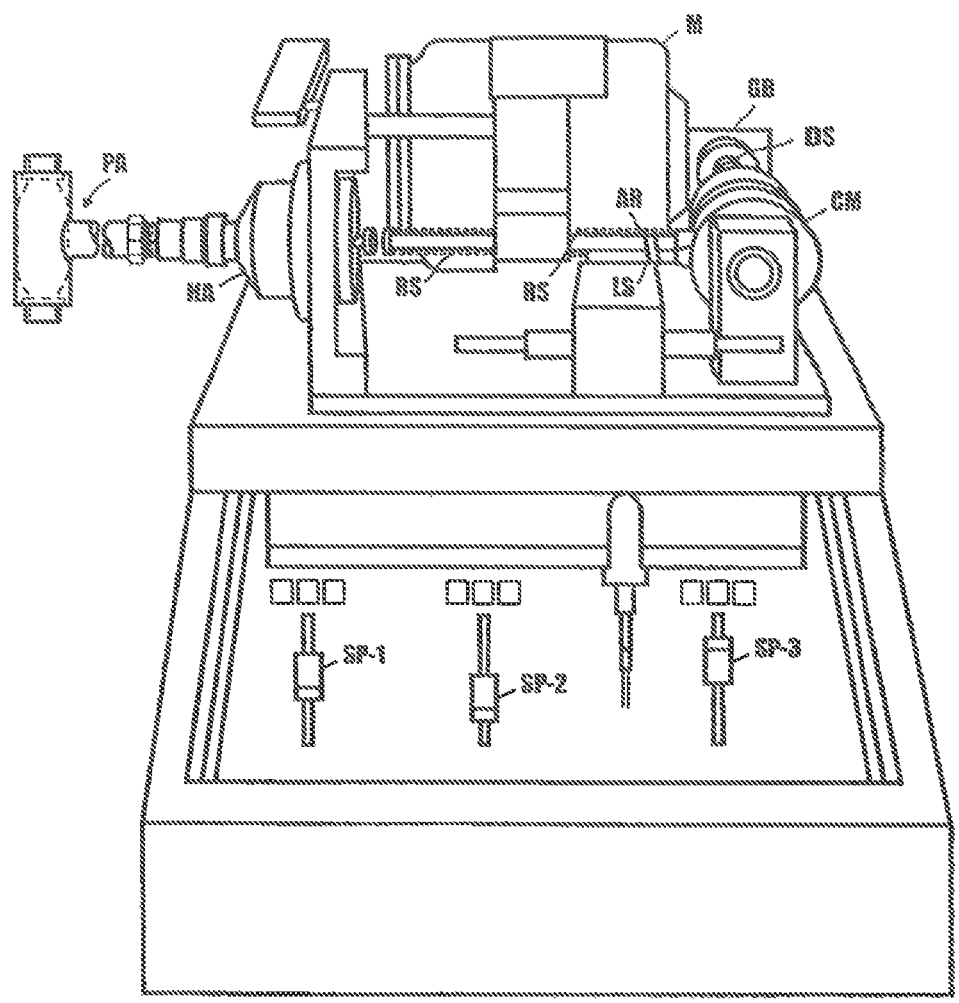
FIG. 1 is a generally perspective view of the prior art pulsatile pump apparatus developed by Dr. McCabe.

Given the absence of methods for quantifying "pulsatile flow" with respect to extracorporeal pumps, new terminology and parameters may be introduced to describe and define accurate physiologic hemodynamic emulation of natural circulatory blood pressure and flow patterns. Such emulation may exhibit benefits similar to those created by natural circulatory systems, that mere loosely defined "pulsatile" technologies do not. In contrast to those, the embodiments herein provide accurate duplication of natural blood pressure and flow patterns as is capable of being represented on a chart recorder or monitor. Such duplication may be accomplished by judicious, independent adjustment of pulse rate, defined as beats/minute, stroke volume, defined as the fluid volume ejected on each stroke, and upstroke rise time, defined as the time interval from stroke start to peak pressure.

A study by Akif Undar, et al. published as "Precise Quantification of Pulsatility is a Necessity for Direct Comparisons of Six Different Pediatric Heart-Lung Machines in a Neonatal CPB Model," ASAIO Journal, 2005, 51:600-603 showed that hemodynamic energy may be a distinguishing parameter between a "Physiologic Pulsatile Pump (PPP)" and other, less life-like systems. Undar and others have confirmed scientifically that the energy gradient or the force of flow makes a very significant difference compared to traditional comparisons of just pressure and flow. Higher energy dramatically increased vital organ flow (lack of good organ flow is associated with ~20% organ damage after bypass alone). The extra energy (or in reality the true physiologic energy) maintains capillary bed patency, which plays an enormous function in cellular oxygenation and waste (metabolite) removal.

Waveform was a specific distinction between pumps evaluated in Undar et al. The shape of the waveform defines accurate physiologic hemodynamic emulation of natural circulatory blood pressure and flow patterns, not mere pressure and flow peaks or averages thereof. Generation of pulsatile flow depends on an energy gradient rather than on a pressure gradient. Waveforms with a more physiological morphology contain more energy when compared with less physiological waveforms at identical pulse pressure and pump flow rates. Extra hemodynamic energy dramatically increases vital organ perfusion under properly controlled pulsatile flow conditions.

Accordingly, embodiments herein may provide methods of accurate physiologic hemodynamic emulation of natural circulatory blood pressure and flow patterns in a pulsatile blood circulating pump system that is adapted for use in extraction of umbilical cord blood and placenta stem cells, regional stem cell therapy including tissue and organ grafting, cardiopulmonary bypass, ventricular assist, ECMO, organ preservation, fetal cardiac bypass, and cancer treatment, plus supporting various areas of circulation research. As used herein, the term "ventricular assist" includes using any of left ventricular assist devices (LVAD), right ventricular assist devices (RVAD), and biventricular assist devices (BiVAD).

Embodiments herein may provide methods wherein a plurality of dynamic characteristics can be controlled in such a way as to produce a blood flow that closely approximates the physiologic natural blood flow of any given patient.

Embodiments herein may provide a pump system of the aforementioned character that can be controlled in such a way as to produce a desired blood flow that closely approximates the physiological blood flow of the patient.

Embodiments herein may provide a pump system as described in the preceding paragraphs that includes a pulsating mechanism having a housing defining a chamber within which a compressible-expandable bladder is sealably mounted and further includes a hydraulic actuator having a pressure imparting chamber with a flexible diaphragm for generating a pulsatile pressure on the transmissive fluid. This, in turn, results in a pulsatile pressure being exerted on the bladder in a manner to controllably vary the volume thereof. Uniquely, a voice-coil actuator, including a compact, highly reliable voice-coil motor and motion controller is operably associated with the hydraulic actuator for controllably moving the pressure imparting member, here provided as a flexible diaphragm.

Embodiments herein may provide a pump system as described in the previous paragraph that further includes a programmable motion controller that controls the voice-coil motor.

Embodiments herein may provide a pump system as described in the preceding paragraphs that further includes a programmable touch-screen component that functions to control the motion controller.

An embodiment includes a physiologic pulsatile pump apparatus that has a pulsatile flow pump with a housing defining a chamber having an inlet port and a disposable, compressible-expandable bladder sealably mounted within the housing. The bladder, which has a receiving port and a delivery port, may be formed from an advanced antithrombogenic material. The physiologic pulsatile pump apparatus also comprises a hydraulic actuator that is connected to the housing of the pulsatile flow pump. The hydraulic actuator, which includes a fluid chamber containing a pressure transmissive fluid, has an outlet port in communication with the inlet port of the pulsatile flow pump housing. A pressure imparting member is mounted within the fluid chamber for movement there within in a manner to generate a pulsatile pressure on the transmissive fluid so as to, in turn, cause a pulsatile pressure to be exerted on the bladder to controllably vary the volume thereof. A voice-coil motor is operably associated with the hydraulic actuator for controllably moving the pressure imparting member within the fluid chamber. Additionally, the physiologic pulsatile pump apparatus includes a fully programmable motion controller for controlling the voice-coil motor and a programmable touch-screen component that functions to control the motion controller.

Figure 2:
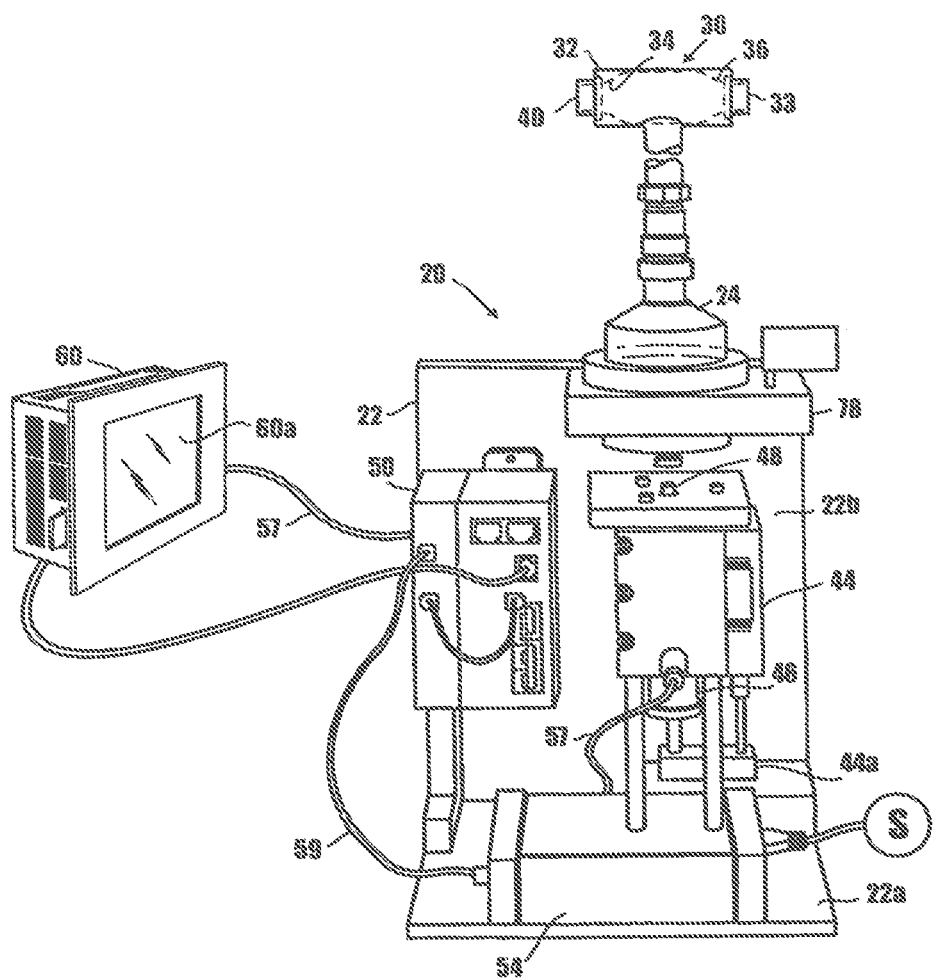
FIG. 2 is a generally perspective view of a physiologic pulsatile pump system according to an embodiment.

Considering first the prior art system illustrated in FIG. 1 of the drawings, this system, which at the time of its development represented a substantial advance in the art, exhibited numerous technological limitations not found in the vastly improved embodiment shown in FIG. 2 of the drawings. For example, the prior art system was analog and, therefore, not programmable. Further, the system variables, including pulse rate, stroke volume and upstroke-rise time were controlled by three separate slide potentiometers "SP-1," "SP-2" and "SP-3" with light emitting diode (LED) read-outs adapted to permit individual control of each variable. In practice, the LED's were hard to read and as they started to fail, frequently caused erroneous readings to occur. Further, in the prior art system, the pulse rate control required an additional three-position multiplier switch to enable it to achieve the full range. Additionally, the slide potentiometer housing of the apparatus undesirably exhibited open space to the interior electronics that could permit fluids, including blood, to reach the interior of the control housing and thereby contaminate the electronics therewithin.

Because of the technological limitations inherent in the prior art system, response time, position control and operational accuracy were limited, trouble-shooting was tedious and diagnostic ability was quite limited.

From a mechanical standpoint, the prior art system as illustrated in FIG. 1 of the drawings was made up of components that were quite bulky, heavy and cumbersome to use and install. The motor "M" of the apparatus, which drove the hydraulic actuator "HA" of the system via a relatively complex clutch mechanism "CM", was a 90 Volt DC motor with brushes that required periodic maintenance. The drive shaft "DS" of the motor was interconnected with a gear box "GB" having a 40:1 gear ratio. Connected to the gearbox at a 90° angle was a custom shaft "DS". Mounted on the shaft "DS" was a custom-made concentric flywheel. Attached to the flywheel was a forwardly extending actuating rod "AR", which on its forward stroke drove the actuating piston of the hydraulic actuator, which was connected to the pump assembly "PA" of the apparatus. Operably associated with the actuating rod were two sets of return springs "RS" that functioned to return the actuating piston to its starting position upon the system electronics releasing the clutch mechanism. Attached to the clutch mechanism "CM" was an adjustable limit switch assembly "LS".

Undesirably, periodic maintenance of the prior art system was required because of continuous wear on the motor brushes, the gearbox and the clutch mechanism. Additionally, the gearbox required periodic maintenance. The clutch mechanism, which was exposed to air, could get dirty, at which time it would malfunction. A dust cover was made to cover the motor/clutch mechanism. Further, the clutch mechanism exhibited a limited life expectancy and replacement of the clutch mechanism would require time-consuming and expensive factory assistance.

Figure 7:
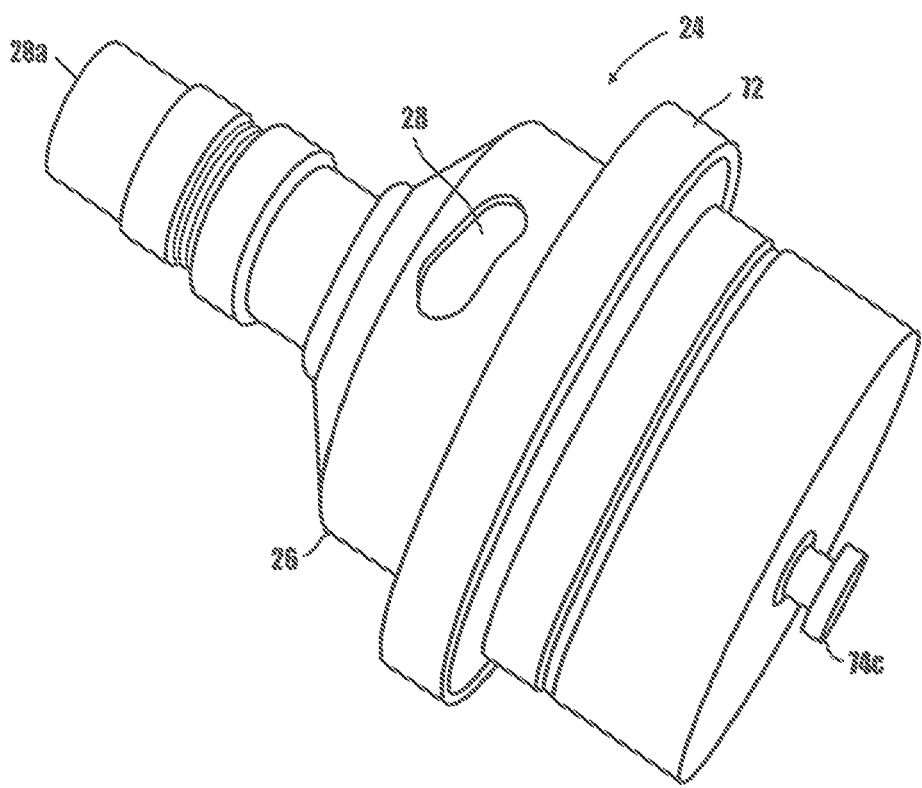
FIG. 7 is a generally perspective view of a hydraulic actuator sub-assembly of the apparatus shown in FIG. 2.
Figure 8:
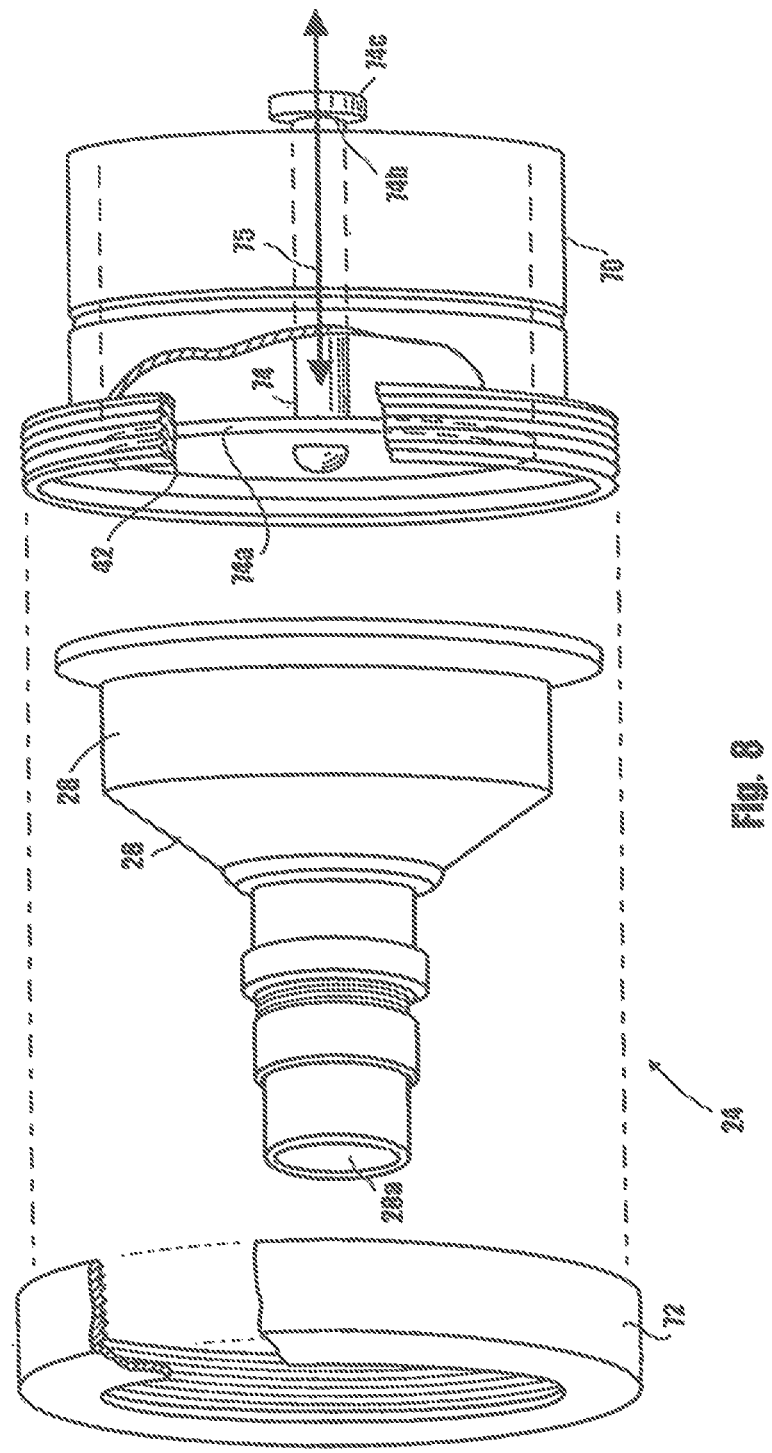
FIG. 8 is a generally perspective, exploded view of the hydraulic actuator sub-assembly shown in FIG. 7.

Referring now to FIG. 2 the drawings, one form of the physiologic pulsatile pump apparatus is there illustrated and generally designated by the numeral 20. This apparatus is adapted for use in accurate physiologic hemodynamic emulation of natural circulatory blood pressure and flow patterns for providing extracorporeal circulation. Examples include, extraction of umbilical cord blood and placenta stem cells, regional stem cell therapy including tissue and organ grafting, cardiopulmonary bypass, ventricular assist (LVAD, RVAD, BiVAD), ECMO, organ preservation, fetal cardiac bypass, and regional cancer treatment. The apparatus includes a support assembly 22 having a base member 22a and a substantially vertical member 22b that is connected to the base member and extends therefrom. The voice-coil actuator motor has one moving part, namely, a shaft moving through a bearing. These types of motors have been running in space applications for over 20 years of continuous operation, and their life expectancy is extended substantially when the motors are mounted in a vertical orientation. Connected to the vertical member 22b is a hydraulic actuator sub-assembly 24 having a housing 26 that defines a fluid chamber 28 having an outlet 28a (FIGS. 7 and 8). The function of this hydraulic actuator sub-assembly will presently be described.

Operably associated with the hydraulic actuator sub-assembly 24 is the pulsatile flow pump 30, which includes a fluid inlet port 30a that is in communication with outlet 28a of the hydraulic actuator sub-assembly in the manner shown in FIG. 2. As will be presently described in greater detail, pulsatile flow pump 30 in cooperation with the actuator sub-assembly 24, functions to generate a pulsatile blood flow that substantially duplicates that of the patient as recorded by a chart recorder.

Figure 9:
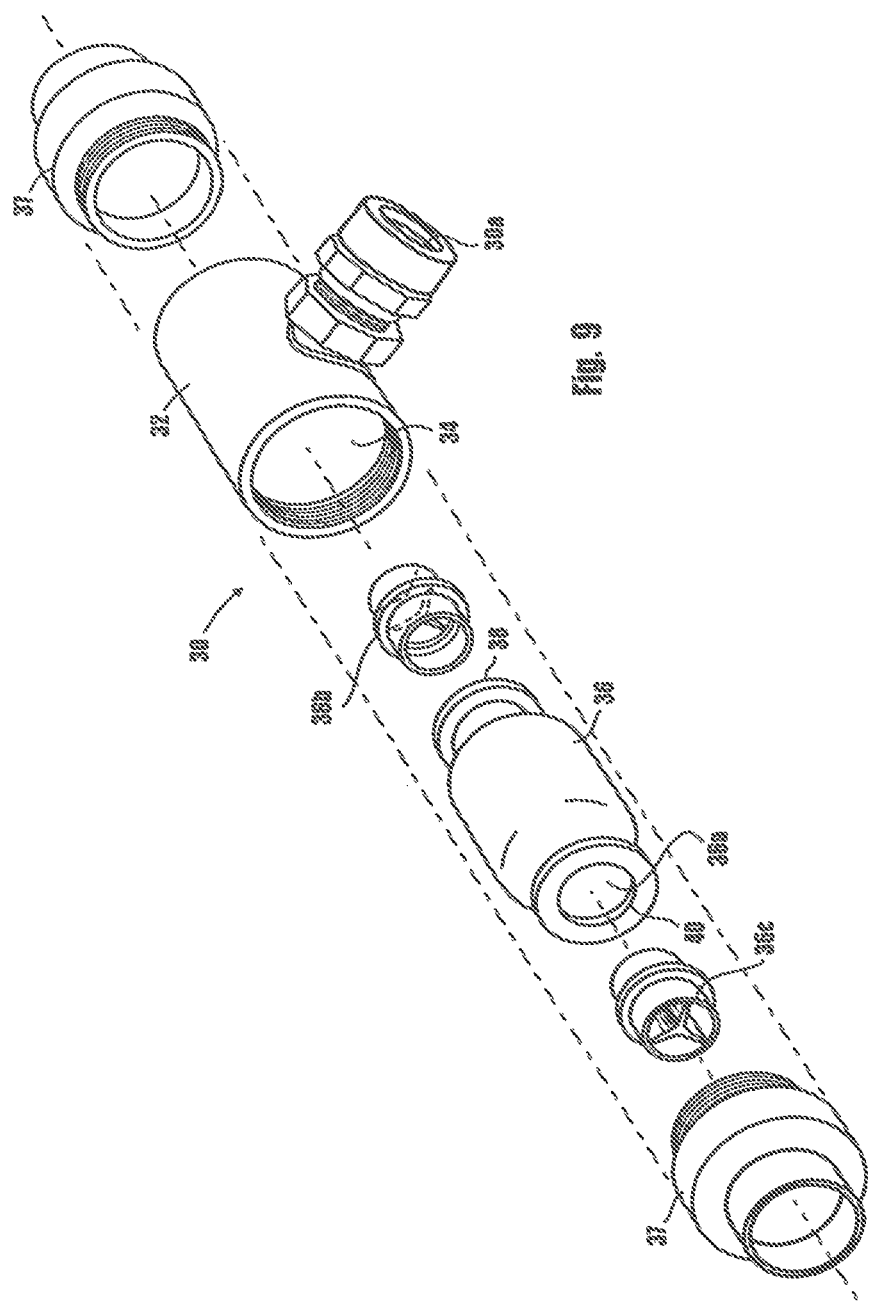
FIG. 9 is a generally perspective, exploded view of a pulsatile pump sub-assembly of the apparatus shown in FIG. 2.

As best seen by referring to FIGS. 2 and 9, mechanism 30 comprises a housing 32 defining a chamber 34 within which is mounted a disposable, compressible-expandable bladder 36 formed from an advanced, antithrombogenic, long-life material. Bladder 36 includes a bladder chamber 36a having a receiving port 38 and a delivery port 40, both of which are in communication with the patient "P" in the manner illustrated in FIG. 10.

As best seen in FIG. 8 of the drawings, sealably mounted within the fluid or actuator chamber 28 of the hydraulic actuator is an actuating member or diaphragm 42 that, during operation of the apparatus, acts upon a pressure transmissive fluid contained within the actuator chamber 28 in a manner to generate a pulsatile pressure on the transmissive fluid. As will be described in greater detail hereinafter, the pulsatile pressure generated on the transmissive fluid by the actuating member 42 results in a pulsatile pressure being exerted on bladder 36 in a manner to controllably vary the volume thereof.

As will be discussed in greater detail hereinafter, operably associated with hydraulic actuator sub-assembly 24 is a voice-coil actuator assembly 44 (FIGS. 2 and 5) that functions to controllably move the actuating member 42 of the hydraulic actuator sub-assembly within the fluid chamber 28 thereof (see FIG. 8). Voice control actuator 44 includes a supporting frame 44a that is connected to substantially vertical member 22b and strategically supports a magnetic voice-coil motor 46 having a reciprocating shaft 48 (FIGS. 5 and 6). In a manner presently to be described, during operation of the apparatus, shaft 48 controllably acts upon actuator member 42 to create the pulsating flow. Voice-coil linear actuator, or motor 46, is readily commercially available from a number of sources, but an actuator offered for sale by H2W Technologies of Valencia, Calif. under the designation NCM10-15-020 and having a stroke of approximately 0.5" (½ inch) has proven quite satisfactory for present purposes. Motor 46 has numerous benefits over the motor of the prior art apparatus illustrated in FIG. 1 of the drawings, including being considerably smaller and lighter, being substantially safer and more reliable in operation, not requiring maintenance and beneficially readily controllable in much the same manner as a known servo-motor. Use of the voice-coil actuator 44 in the present apparatus renders unnecessary the dual 90° angled shafts, the concentric fly wheel, the gearbox, the difficult-to-service electromagnetic clutch, and return springs of the previously described prior art apparatus illustrated in FIG. 1.

Figure 4:
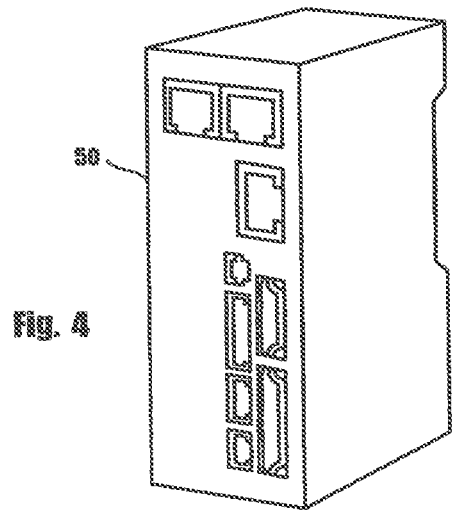
FIG. 4 is a generally perspective view of a programmable motion controller component of the apparatus shown in FIG. 2.

Also connected to vertical support member 22b of support 22 is a motion controller 50 that is operably associated with the voice-coil motor 46 for precisely controlling the motor (see FIGS. 2 and 4). A suitable motion controller 50, which is of known construction, is readily available from several sources, including the Elmo USA Company of Westford, Mass. Motion controller 50 may include a readily programmable, state-of-the-art digital control system, provide closed-loop linear position control, and utilize RS-232 communication, that is a recommended form of serial communication through a computer to control hardware such as the voice-coil actuator 46. Beneficially, motion controller 50 provides fast response time, accurate position control and permits remote trouble-shooting capability. Additionally, limit controls can be accurately programmed into the electronics of the controller with selected read-outs, if desired, thereby providing a high degree of safety during operation of the apparatus.

When compared to the prior art apparatus shown in FIG. 1 of the drawings, it is abundantly clear that the use of motor controller 50 provides substantially greater safety, greater reliability and superior compatibility with and control over cooperating operating components, such as the hydraulic actuator driving motor, the EKG-trigger and like peripherals.

As illustrated in FIG. 2 of the drawings, to provide electrical power to the motor 46 and to the motion controller 50, a known power supply 54 is suitably mounted on the horizontal member 22a of the support assembly 22 and is connected to a suitable source of power "S". A suitable power supply 54 is readily commercially available from a number of sources, including the previously identified H2W Technologies of Valencia, Calif. Suitable cabling, including cables 57 and 59, interconnect the power supply with the motor 46 and the motion controller 50.

Figure 3:
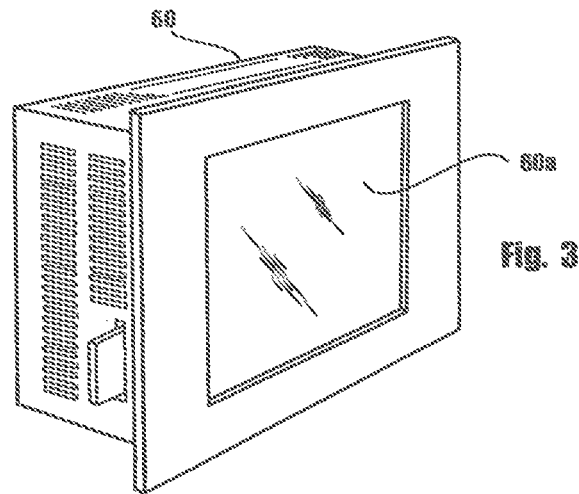
FIG. 3 is a generally perspective view of a touch-screen component of the apparatus shown in FIG. 2.

Operably associated with motion controller 50 via a connector 51 is a touch-screen unit 60 (FIGS. 2 and 3). A suitable touch-screen unit 60, which may include desired color read-outs, is readily commercially available from a number of sources including the ESA Technology Company of Windsor, Calif. Touch-screen unit 60 here comprises a state-of-the-art touch-terminal that greatly simplifies the operation and control of the interactive components of the apparatus. The touch-screen unit includes a rugged touch-screen 60a upon which graphic images in various formats, such as those illustrated in FIGS. 12 and 13 can be imported. During operation of the apparatus, the read-outs on the touch-screen 60a that are easy to see can be quickly and precisely changed on-the-fly and, in a manner presently to be discussed, automatically activate with an EKG signal. When compared with the apparatus of the prior art as illustrated in FIG. 1 of the drawings, the apparatus that includes the cooperatively associated motion controller 50 and the touch-screen unit 60, permits significantly greater control of pulse rate, stroke volume, and upstroke-rise time as well as providing much more precise resolution.

Figure 11:
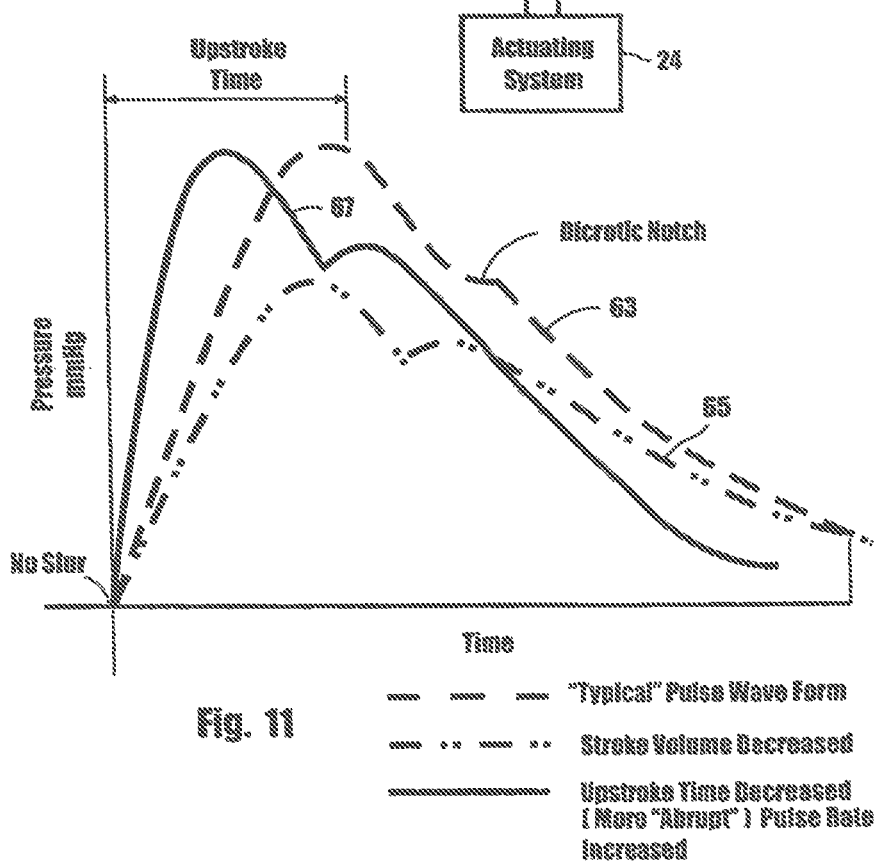
FIG. 11 is a generally diagrammatic view illustrating a set of blood-pressure curves.

The embodiments described in the preceding paragraphs are designed to accurately duplicate a blood pressure curve by independently varying pulse rate, that is the number of beats per minute; stroke volume, that is the volume of blood pumped on each beat, and upstroke-rise time, that is the duration of time from the start to peak pressure at the top of the curve on each beat. In a potential clinical application, as for example, a cardiopulmonary bypass procedure or an organ preservation procedure, this duplication of the blood pressure curve can be achieved by a method that includes the following steps. The first step in the process is to obtain in a known manner a blood pressure chart recorder tracing from the patient or organ being treated. The dotted lines 63 of FIG. 11, which is a plot of pressure versus time, illustrates a pulse wave-form. Using this information, the pulse rate and upstroke-rise time can be calculated and programmed into the touch-screen unit 60 in a manner well understood by those skilled in the art (see FIGS. 12 and 13). The dotted lines 65 of FIG. 11 of the drawings illustrate a stroke volume decrease, while the solid line 67 illustrates a decrease in upstroke time.

With the forgoing in mind, the basic design theory of the embodiments is that once the pulse wave and flow patterns are duplicated, pressure and flow may be controlled by the peripheral resistance of the blood vessels, there may be no variance in blood pressure/flow patterns; the capillary beds (microcirculation) may be filled and flushed with a full flow of blood; there may be normal oxygenation of all tissues; and all waste products (metabolites) may be effectively removed. In addition, the pulsatile flow created by the apparatus has been proven to be vastly superior to non-pulsatile flow and non-physiologic "pulsatile flow" created by other types of prior art apparatus. Based on a study of 194 related articles published between 1952 and 2006, it has been determined that pulsatile flow decreased the incidence of post-operative deaths in pediatric and adult patients, significantly increased blood flow of vital organs including brain, heart, liver, and pancreas, reduced systemic inflammatory response syndrome, significantly increased vital organ recovery in several types of animal models when compared to non-pulsatile perfusion and generates more hemodynamic energy, which better maintains the microcirculation compared with non-pulsatile flow. It has also been determined that infants receiving pulsatile blood flow during bypass surgery awakened more quickly, were more alert and required less post-operative ventilation.

The various components of the apparatus are assembled together in a manner illustrated in FIG. 2 of the drawings. In this regard, the hydraulic actuating unit 24 is first assembled in the manner indicated in FIG. 8 of the drawings by operably interconnecting the housing 26 with the actuator base 70 using the threaded connector ring 72. Actuator base 70 houses the previously mentioned diaphragm 42 which is interconnected with an operating shaft 74 that is reciprocally movable within base 70 in the manner indicated by the arrow 75 of FIG. 8. Next, the assembled actuating unit 24 is mounted within a capture plate 78 that is interconnected with vertical support member 22b in the manner shown in FIG. 2 of the drawings. This done, the fluid reservoir or chamber 28 of the actuating unit, is filled with a suitable pressure transmissive fluid.

With the actuating unit 24 properly mounted on the support structure in the manner shown in FIG. 2, the pulsatile flow pump 30 is interconnected with the actuating unit so that the inlet 30a of the mechanism is in fluid communication with outlet 28a of the actuating unit and is in fluid communication with the fluid reservoir or chamber 28 of the actuating unit.

Figure 10:
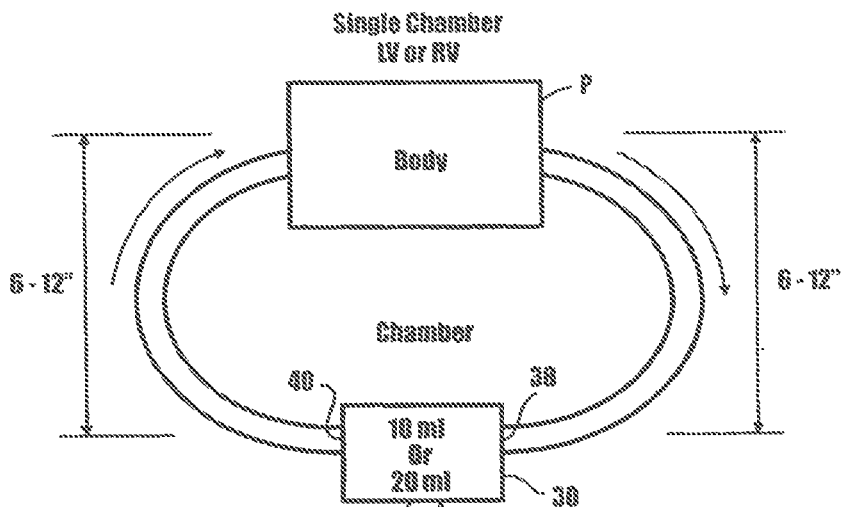
FIG. 10 is a generally diagrammatic view illustrating the manner of interconnection of the hydraulic actuator sub-assembly and the pulsatile pump sub-assembly with a patient.

As previously mentioned and as indicated in FIGS. 2 and 9 of the drawings, the compressible-expandable bladder 36 of the pulsatile flow pump is centrally disposed within chamber 34 of housing 32 so that the receiving and delivery ports 38 and 40 thereof extend outwardly from housing 32 to enable them to be interconnected with the patient in the manner illustrated in FIG. 10.

Figure 12:
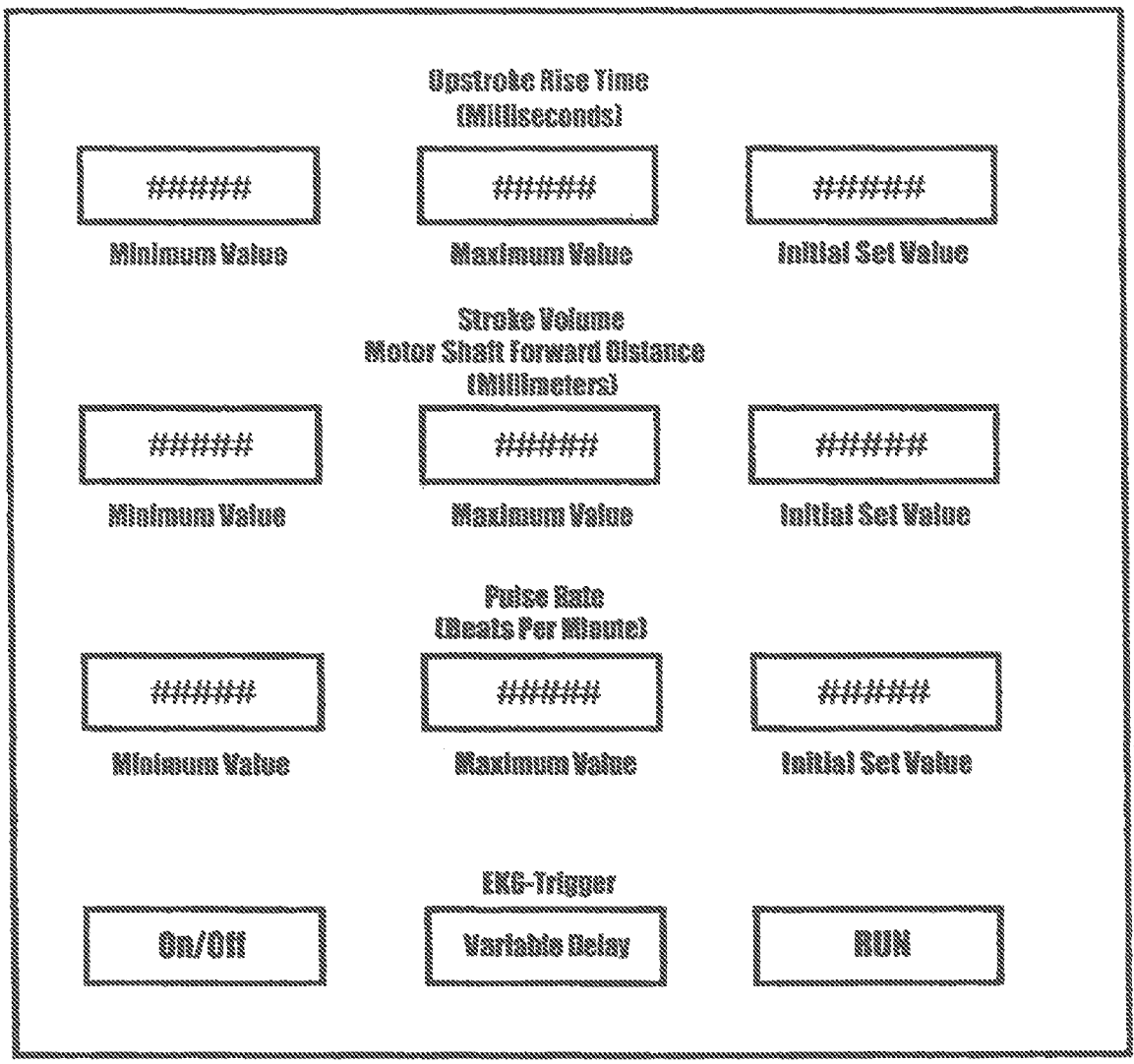
FIG. 12 is a generally diagrammatic view illustrating one type of image that appears on a touch-screen sub-assembly of the apparatus shown in FIG. 2.
Figure 13:
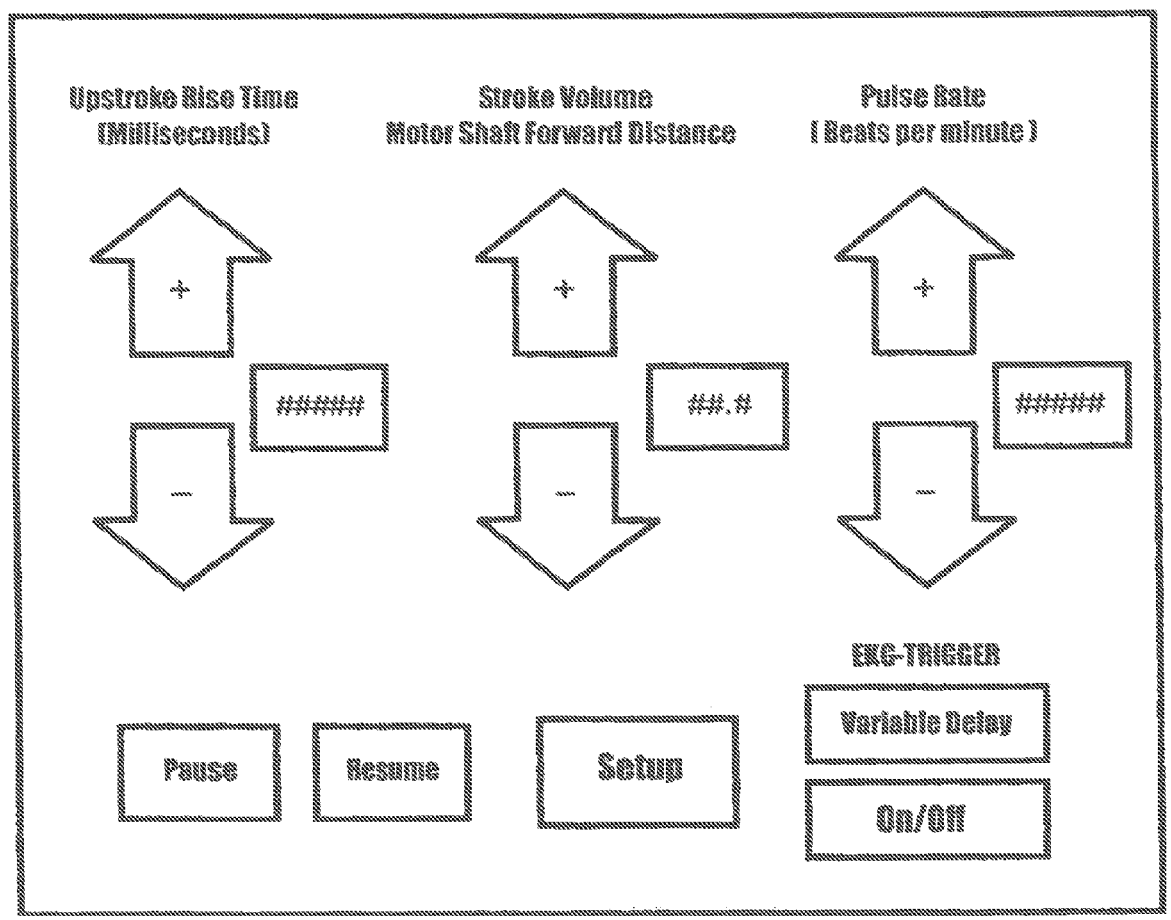
FIG. 13 is a generally diagrammatic view illustrating another type of image that appears on the touch-screen sub-assembly of the apparatus shown in FIG. 2.

Following the programming of the motion controller and the touch-screen unit in a manner well understood by those skilled in the art, the pumping or perfusion step is commenced by manipulating the stroke volume control image appearing on the touch-screen in a manner such that the blood pressure curve matches the chart recorder blood pressure reading obtained from the patient (see for example, FIGS. 12 and 13). Other applications, such as ventricular assist (LVAD, RVAD, BiVAD), ECMO, etc., may have different perfusion parameters and the present system is uniquely able to adapt to each application.

As previously mentioned, the pumping or perfusion step is accomplished by the cooperative interaction of the hydraulic actuator sub-assembly 24 and the pulsatile flow pump 30. In this regard as illustrated in FIG. 8, the hydraulic actuator sub-assembly 24 includes a reciprocating shaft 74 that is interconnected with diaphragm 42 at one extremity 74a and has, at its other extremity 72b, an enlarged diameter head portion 74c that is acted upon by shaft 48 of the voice control motor 46 as the motor shaft reciprocates under the control of the motion controller 50.

As shaft 74 of the actuator sub-assembly 24 reciprocates, diaphragm 42 acts upon a pressure transmissive fluid contained within the actuator chamber 28 in a manner to generate a pulsatile pressure on the transmissive fluid. The pulsatile pressure generated on the transmissive fluid in turn results in a pulsatile pressure being exerted on bladder 36 in a manner to controllably vary the volume thereof. As the bladder 36 is collapsed by the pressure exerted on the bladder by the pressure transmissive fluid, blood is forced outwardly of the delivery port 40 of the bladder 36 and through the novel tricuspid valve 36c that is mounted within the delivery port (FIG. 9). Conversely, a reduction in pressure of the transmissive fluid caused by a retraction of the reciprocating shaft 48 permits the compressible-expandable bladder 36 to expand in a manner to allow highly desirable positive pressure/passive infilling via the inflow or receiving port 38 via the tricuspid valve 36b that is mounted within the port (see FIGS. 9 and 10).

Tricuspid valves 36b and 36c, which are held in position by threaded connectors 37, uniquely mimic the shape and action of the native tricuspid heart valve, which is located on the right side of the heart between the right atrium and the right ventricle. During normal operation of the heart, the right atrium receives deoxygenated blood from the superior and inferior vena cavae and the coronary sinus and pumps it into the right ventricle through the heart's tricuspid valve.

Continued operation of the pulsatile flow pump 30, the hydraulic actuator sub-assembly 24 and voice-coil motor 46, which is under the control of the motion controller 50, may generate a physiologic pulsatile blood flow that very accurately duplicates blood pressure and flow patterns of the patient while handling the patient's blood gently.

When the apparatus is used to partially support a beating heart in carrying out procedures such as ventricular assist and Extracorporeal Membrane Oxygenation (ECMO), a certain timing of each beat of the pump is beneficial. In this regard, medical research has shown that a pump system that is assisting a beating heart may beneficially trigger shortly after the actual heart beat. Pumping at the same time actually puts an additional load on the heart. The variable delay allows the exact desired time interval to be set which gives optimal healing. Each beat shows two pressure peaks on the monitor.

Figure 14:
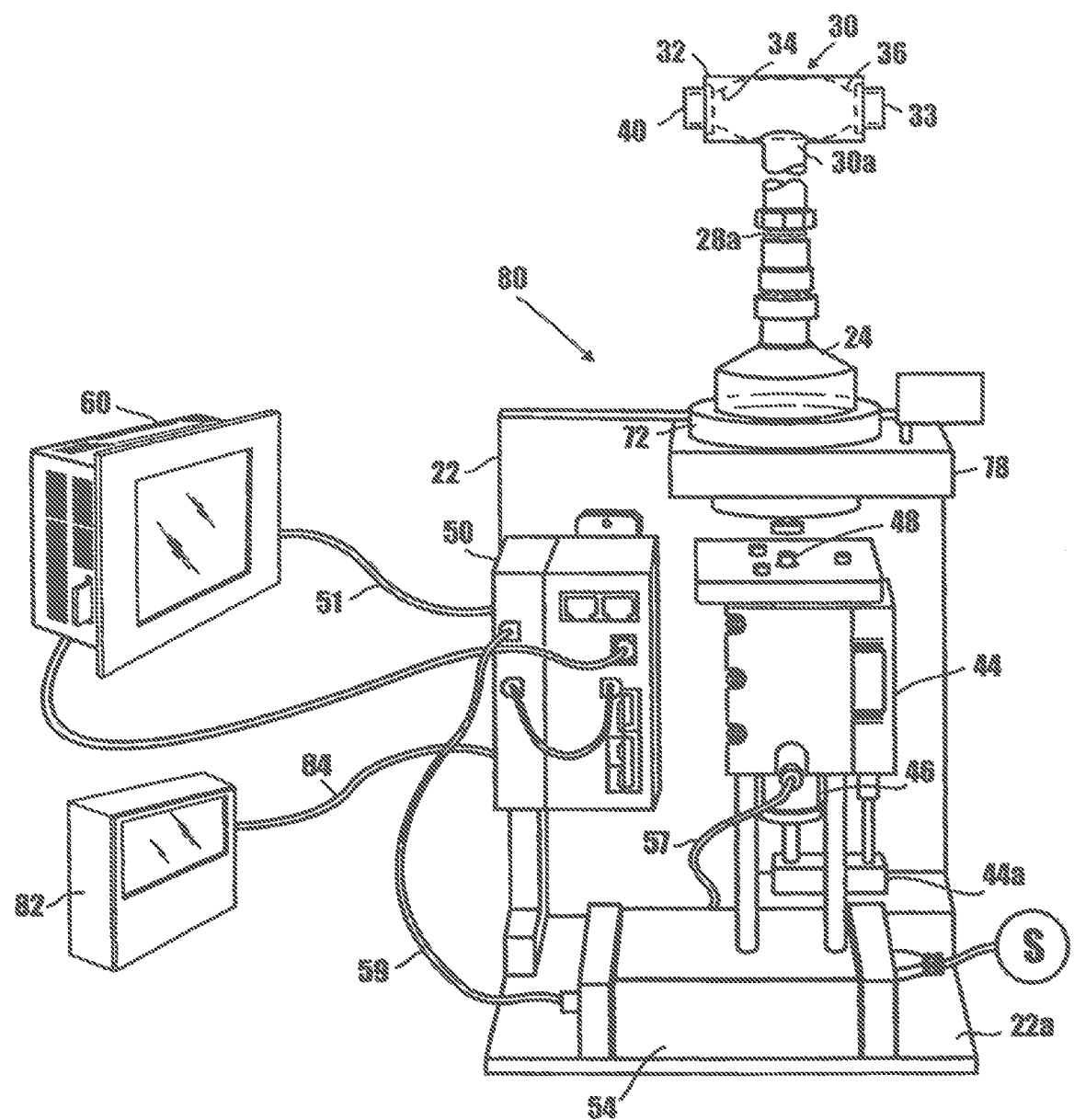
FIG. 14 is a generally perspective view of a physiological pulsatile pump system according to another embodiment.

In accomplishing the procedures identified in the preceding paragraph, an alternate form of the apparatus may be used. This alternate form of the apparatus, which is illustrated in FIG. 14 of the drawings and is generally designated by the numeral 80, uniquely includes an EKG-trigger circuit. This alternate form of the apparatus is similar in most respects to that illustrated in FIGS. 2 through 13 and like numerals are used in FIG. 14 to identify like components. An EKG unit 82 is interconnected with the motion controller 50 by means of a suitable cable 84. With this construction, during the accomplishment of the operational procedure, the system can be triggered by an electronic EKG signal obtained from the patient's heart so that that the mechanism 30 beats every time the patient's heart beats. In some laboratory studies, when a heart was removed and placed on an oxygen preservation perfusion machine, the heart continued to beat out of the body (ex vivo). That application may also use an EKG-trigger with a variable delay. In this alternate form of the apparatus, when the EKG-trigger is activated, the trigger uniquely overrides the pulse rate control on the touch-screen 60 (see FIG. 13). The EKG-trigger and variable delay are built-in to the electronics, and are controlled on the touch-screen with read-outs. In the prior art system, the EKG unit was a later "add-on" and thus was an additional external circuit that acted as a relay between patient and the pump system. In the prior art unit there were more cords, no read-out of the delay and the unit could only be activated by flipping a switch on the back of the pump as compared to an automatic override on the new system.

Figure 15:
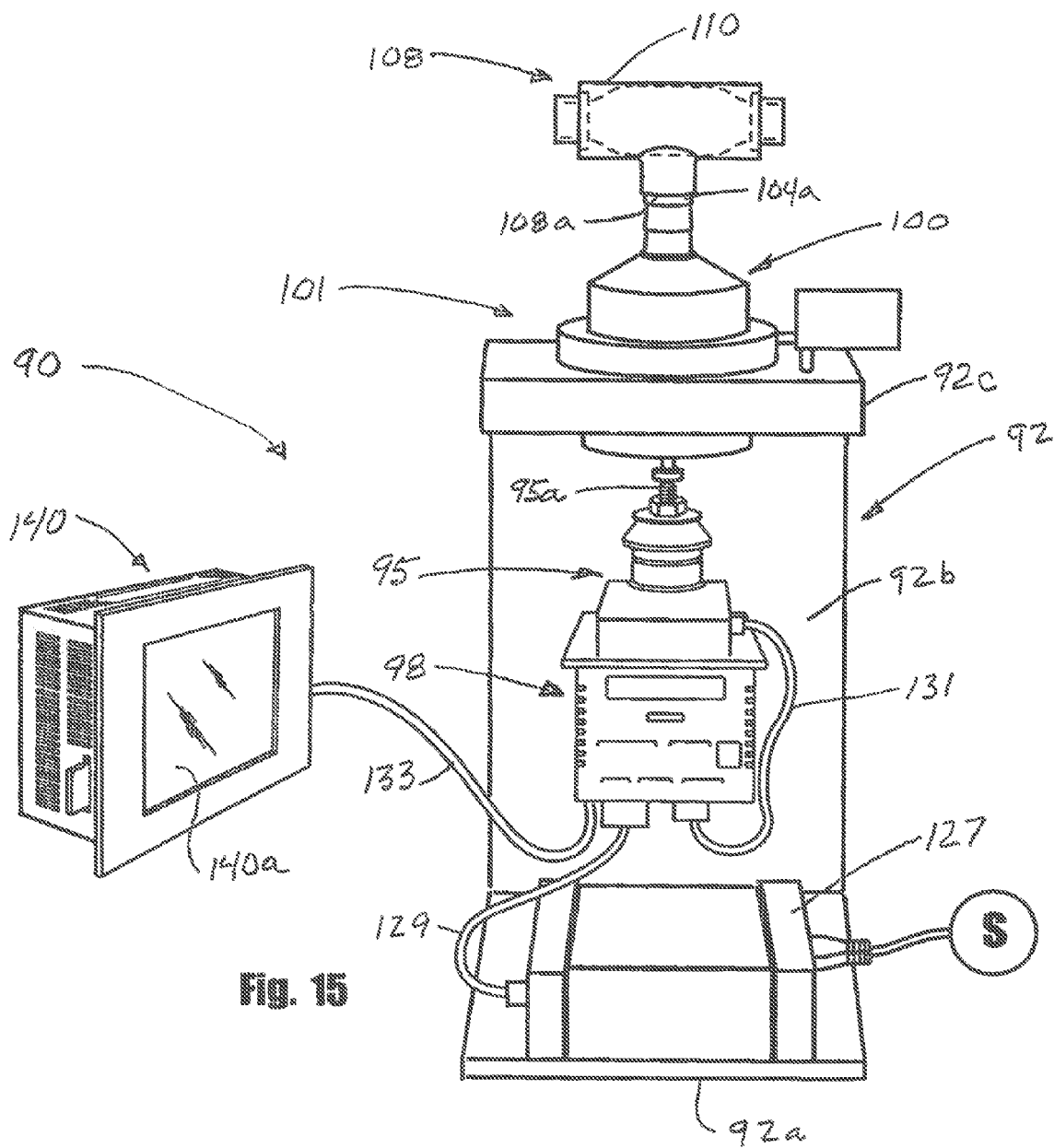
FIG. 15 is a generally perspective view of a physiological pulsatile pump system according to a further embodiment.
Figure 16:
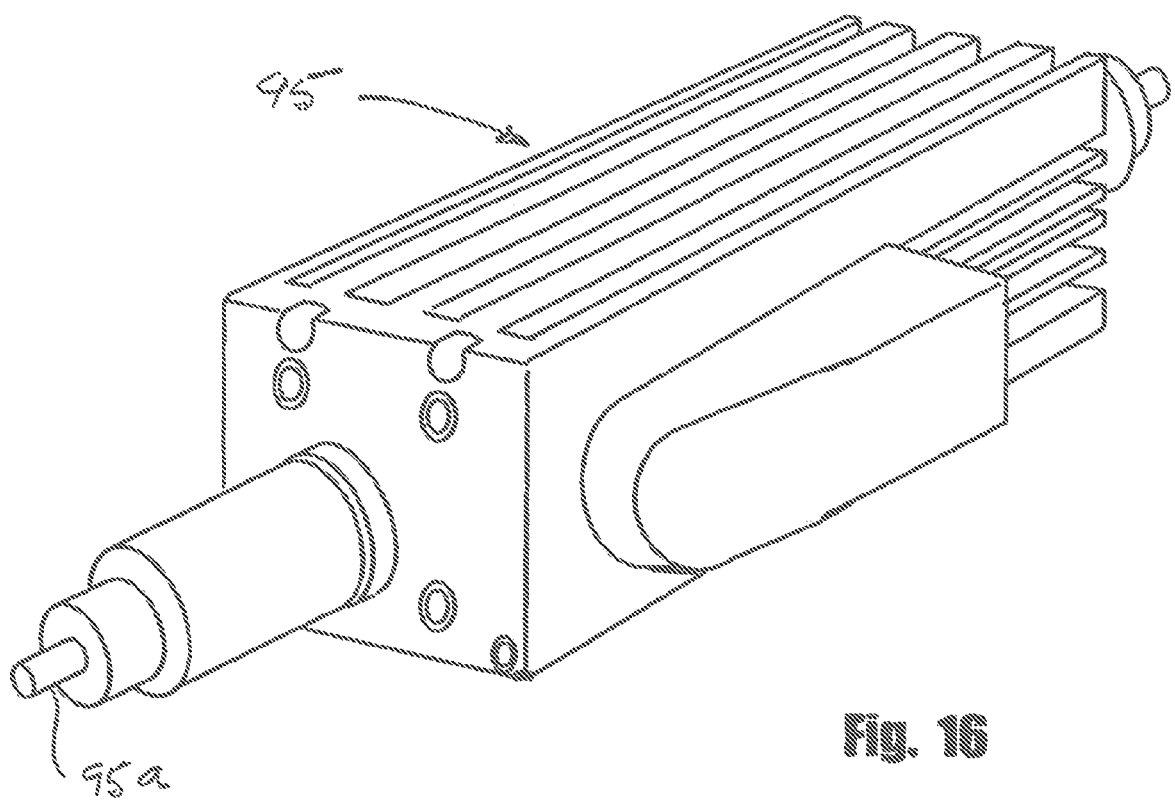
FIG. 16 is a generally perspective view of a motor of the apparatus shown in FIG. 15.

Referring now to FIG. 15, still another form of the physiologic pulsatile pump apparatus is there illustrated and generally designated by the numeral 90. This latest form of the apparatus is also similar in many respects to that illustrated in FIGS. 2 through 13 and like numerals are used in FIG. 15 to identify like components. Apparatus 90, which is also adapted for use in extraction of umbilical cord blood and placenta stem cells, regional stem cell therapy including tissue and organ grafting, cardiopulmonary bypass, ventricular assist (LVAD, RVAD, BiVAD), ECMO, organ preservation, fetal cardiac bypass, regional cancer treatment, and various areas of circulation research, here comprises a support assembly 92 having a base member 92a and a substantially vertical member 92b that is connected to the base member and extends therefrom. The actuator motor system 95, which is attached to member 92b in the manner shown in FIG. 15, is of a different construction from the voice-coil actuator motor of the previously described embodiments. The voice-coil system of the previously described embodiments is a non-communicating system that comprises a motor that includes a piston, or shaft, that moves back and forth through a dedicated stroke. In sharp contradistinction, the actuator motor system 95, the construction of which is illustrated in FIG. 16, comprises a servo system, which beneficially is a fully communicating system. Motor system 95 may be of the type manufactured by Dunkermotoren USA Inc. of Elgin, Ill. and sold under the designation "STA 2506". In using this motor system, constant monitoring of the position and velocity of the piston 95a is possible, thereby permitting more accurate control for superior results. The details of the construction and operation of this novel motor system are available from Dunkermotoren USA Inc. In a manner presently to be described, during operation of the apparatus, piston or shaft 95a controllably acts upon the actuator member of the apparatus to create the pulsating flow.

Operably associated with and adapted to control motor system 95 is a motion controller system 98. A suitable system is available from Copley Controls. This novel controller system, which is sold under the name and style "XENUS Micro", is a compact, AC power servo drive for continuously monitoring and controlling the movement of the shaft 95a of the actuator motor system. Motion controller system 98, which is mounted on motor system 95 (see FIG. 15), continuously monitors and controls the position, velocity, and torque of the shaft of the motor system. The details of the construction and operation of this novel controller system are available from Copley Controls. Motor system 95 and controller system 98, along with a hydraulic actuating sub-assembly 100, the character of which will presently be described, comprise the actuator system 101 that operates the pulsatile flow pump.

The hydraulic actuating sub-assembly 100, which is of a somewhat different construction from the previously described hydraulic actuator sub-assembly 24, is connected to a horizontal support member 92c that is connected to the vertical member 92b in the manner shown in FIG. 15 of the drawings. As best seen in FIG. 16, hydraulic actuator sub-assembly 100 includes a housing 102 that defines a fluid chamber 104 having an outlet 104a. The function of this alternate form of hydraulic actuating sub-assembly will presently be described.

Figure 19:
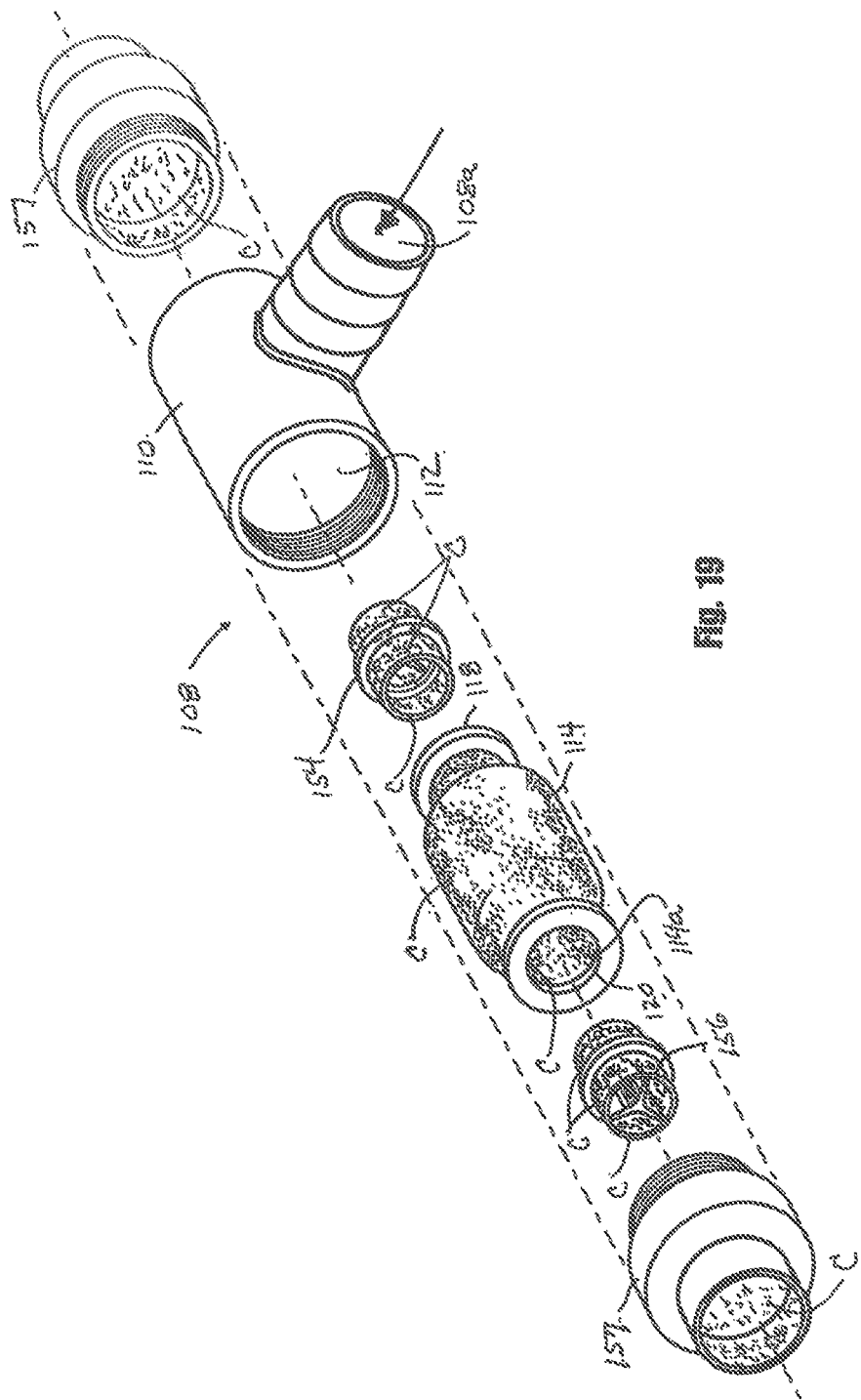
FIG. 19 is a generally perspective, exploded view of a pulsatile pump sub-assembly of the apparatus shown in FIG. 15.

Operably associated with the hydraulic actuating sub-assembly 100 is the pulsatile flow pump 108, which is also of a slightly different construction from that earlier described. As indicated in FIG. 19 of the drawings, pump 108 includes a fluid inlet port 108a that is in communication with outlet 104a of the hydraulic actuating sub-assembly in the manner shown in FIG. 15. As will be presently described in greater detail, pulsatile flow pump 108 in cooperation with the actuating sub-assembly 100, functions to generate a pulsatile blood flow that substantially duplicates that of the patient as recorded by a chart recorder.

As best seen by referring to FIGS. 15 and 19, pump 108 comprises a housing 110 defining a chamber 112 within which is mounted a disposable, compressible-expandable bladder 114 formed from a carbothane thermoplastic elastomer. This material is highly beneficial for the present application because it does not cause blood damage (hemolysis) and exhibits good biocompatible and mechanical properties. Bladder 114 includes a bladder chamber 114a having a receiving port 118 and a delivery port 120, both of which are in communication with the patient "P" in the manner illustrated in FIG. 20. As indicated in FIG. 19 of the drawings, the surfaces of the bladder are coated with a proprietary coating "C" that is produced by AllvivoVascular, Inc. of Lake Forest, Calif. This coating material, the details of which are available from AllvivoVascular, Inc., uniquely protects against thrombus and significantly reduces systematic inflammatory response which occurs in about 1% of pediatric heart patients.

Figure 18:
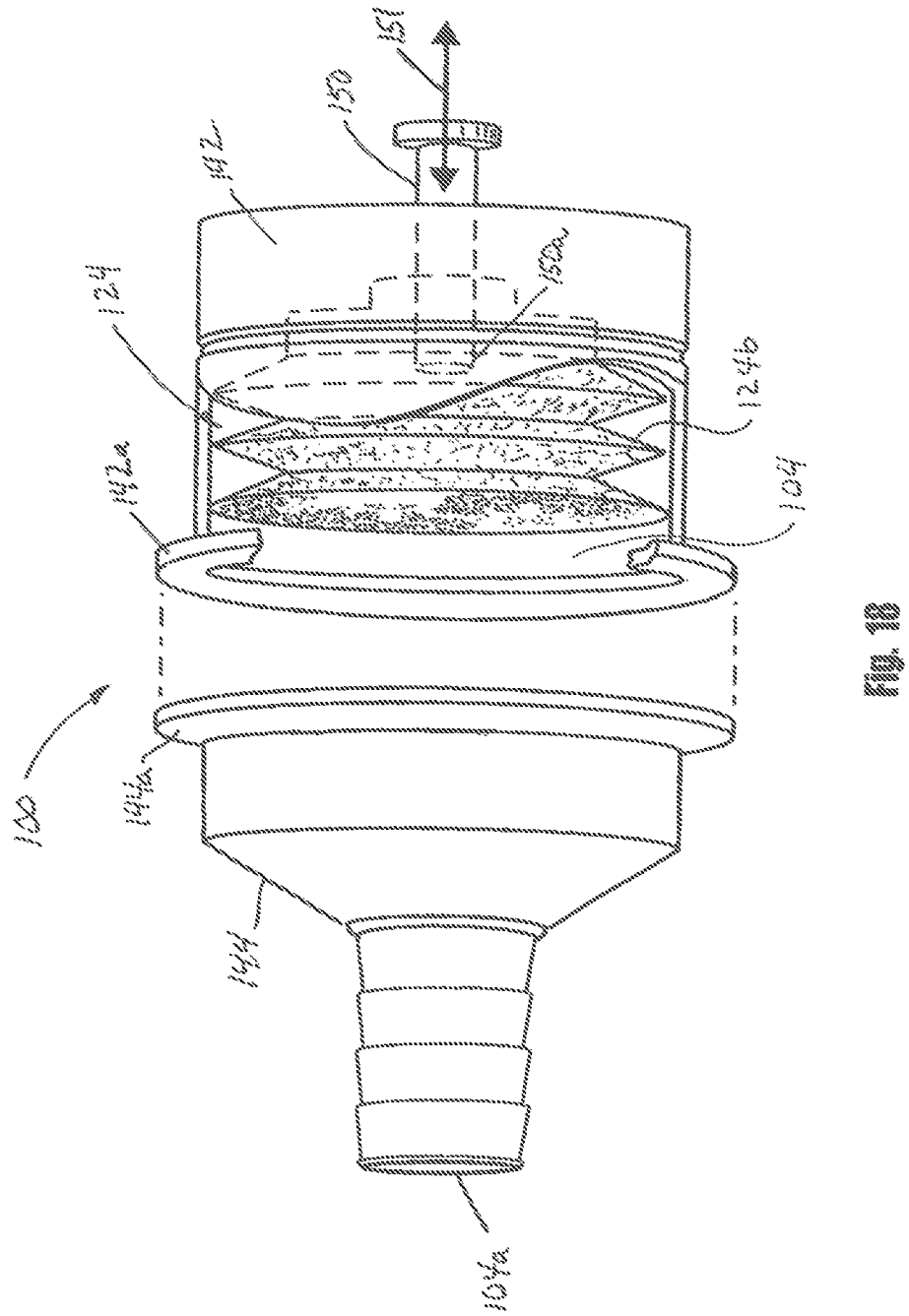
FIG. 18 is a generally perspective, exploded view of the hydraulic actuator sub-assembly shown in FIG. 17.

As best seen in FIG. 18 of the drawings, sealably mounted within the fluid actuator chamber 104 of the hydraulic actuator sub-assembly 100 is a bellows type actuating member or diaphragm 124 which, during operation of the apparatus, acts upon a pressure transmissive fluid contained within the actuator chamber 104 in a manner to generate a pulsatile pressure on the transmissive fluid. A suitable diaphragm 124 that is of a unique construction having a base 124a and a bellows-like side wall 124b is commercially available from the Vi-Cas Mfg Company of Cincinnati, Ohio. As will be described in greater detail hereinafter, the pulsatile pressure generated on the transmissive fluid by the actuating member 124 results in a pulsatile pressure being exerted on bladder 114 in a manner to controllably vary the volume thereof.

As previously discussed, motor system 95, which is operably associated with hydraulic actuator sub-assembly 114, functions to controllably move the actuating member 124 of the hydraulic actuating sub-assembly within the fluid chamber 104 thereof (see FIG. 18).

As illustrated in FIG. 15 of the drawings, to provide electrical power to the motor system 95 and the controller system 98, a known power supply 127 is suitably mounted on the horizontal member 92a of the support assembly 92 and is connected to a suitable source of power "S". Power supply 127 is readily commercially available from a number of sources, including the previously identified H2W Technologies of Valencia, Calif. Suitable cabling, including cables 129 and 131, interconnect the power supply with the motor system 95 and the controller system 98.

Operably associated with the controller system 98 via a connector 133 is a touch-screen unit 140 (FIG. 15). A suitable touch-screen unit 140, which forms a part of the actuator system 101, that includes desired color read-outs is readily commercially available from a number of sources including the ESA Technology Company of Windsor, Calif. Touch-screen unit 140 here comprises a state-of-the-art touch-terminal that greatly simplifies the operation and control of the interactive components of the apparatus. The touch-screen unit includes a rugged touch-screen 140a upon which graphic images in various formats can be imported. During operation of the apparatus, the read-outs on the touch-screen that are easy to see can be quickly and precisely changed on-the-fly and, in a manner presently to be discussed, automatically activate with an EKG signal.

As in the earlier described embodiments, the apparatus is designed to accurately duplicate a blood pressure curve by independently varying pulse rate, that is the number of beats per minute; stroke volume, that is the volume of blood pumped on each beat; and upstroke-rise time, that is the duration of time from the start to peak pressure at the top of the curve on each beat. In a potential clinical application as, for example, a cardiopulmonary bypass procedure or an organ preservation procedure, this duplication of the blood pressure curve can be achieved by a method that includes the following steps. The first step in the process is to obtain, in a known manner, a blood pressure chart recorder tracing from the patient or organ being treated. The dotted lines 63 of FIG. 11 of the drawings, which is a plot of pressure versus time, illustrates a pulse wave-form. Using this information, the pulse rate and upstroke-rise time can be calculated and programmed into a touch-screen unit such as unit 140 (FIG. 15) in a manner well understood by those skilled in the art (see FIGS. 12 and 13). The dotted lines 65 of FIG. 11 of the drawings illustrate a stroke volume decrease, while the solid line 67 illustrates a decrease in upstroke time.

With the forgoing in mind, the basic design theory of the apparatus is that once the pulse wave and flow patterns are duplicated, pressure and flow may be controlled by the peripheral resistance of the blood vessels, there may be no variance in blood pressure/flow patterns; the capillary beds (microcirculation) may be filled and flushed with a full flow of blood; there may be normal oxygenation of all tissues; and all waste products (metabolites) may be effectively removed.

The various components of the apparatus are assembled together into the configuration illustrated in FIGS. 15 and 20 of the drawings. In this regard, the hydraulic actuating sub-assembly 100 is first assembled in the manner indicated in FIG. 17 of the drawings so that the bellows type actuating member or diaphragm 124 is properly secured within base portion 142. With the bellows type actuating member in position within base portion 142 and with the operating shaft 95a of the motor system properly interconnected with the actuating member 124, the flange portion 142a of the base portion 142 is sealably connected to the flange portion 144a of the top portion 144 by any suitable means such as, by way of example, adhesive bonding.

Figure 17:
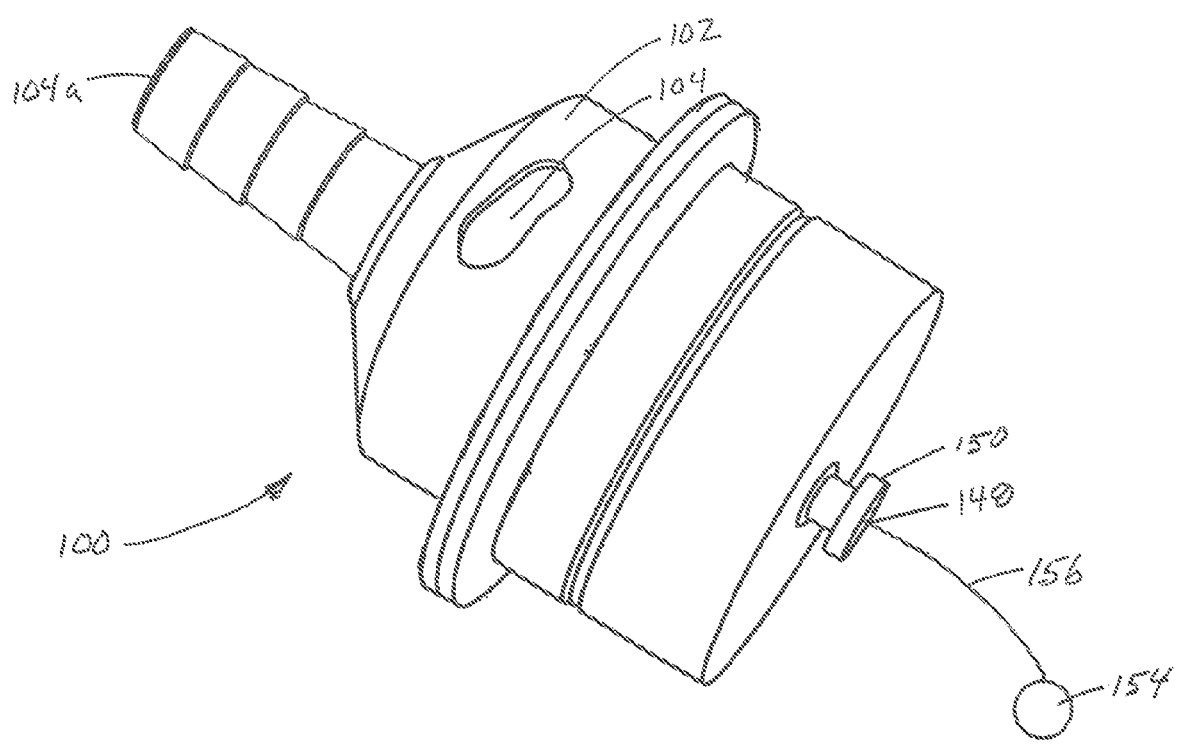
FIG. 17 is a generally perspective view of a hydraulic actuator sub-assembly of the apparatus shown in FIG. 15.

Following its assembly, the actuating sub-system 100 is connected to horizontal support member 92c in the manner shown in FIG. 15 of the drawings. Next, the pulsatile flow pump 108 is interconnected with the system so that the inlet 108a of the pump is in fluid communication with outlet 104a of the actuating sub-system. With the pulsatile flow pump 108 interconnected with the system in the manner shown in FIG. 15, the fluid reservoir, or chamber 104 of the actuating sub-system, as well as the bladder chamber 114a of the bladder 114 of the pulsatile flow pump 108, is filled with a suitable pressure transmissive fluid via a fill port 148 (FIG. 17), fill port 148 provided in an operating shaft 150 that is reciprocally movable within base 142 in the manner indicated by the arrow 151 of FIG. 18. As illustrated in FIG. 17, fill port 148 is connected with a source of transmissive fluid 154 via a fill line 156.

As previously mentioned, and as indicated in FIG. 19 of the drawings, the compressible-expandable bladder 114 of the pulsatile flow pump is centrally disposed within chamber 112 of housing 110 so that the receiving and delivery ports 118 and 120 thereof extend outwardly from housing 110 to enable them to be interconnected with the patient in the manner illustrated in FIG. 20.

Following the programming of the motion controller and the touch-screen unit in a manner well understood by those skilled in the art, the pumping or perfusion step is commenced by manipulating the stroke volume control image appearing on the touch-screen in a manner such that the blood pressure curve matches the chart recorder blood pressure reading obtained from the patient (see for example, FIGS. 12 and 13). Other applications such as ventricular assist (LVAD, RVAD, BiVAD), ECMO, etc., may have different perfusion parameters and the present system is uniquely able to adapt to each application.

As previously mentioned, the pumping or perfusion step is accomplished by the cooperative interaction of the pulsatile flow pump 108 and the actuator system 101 and by the hydraulic actuating sub-assembly 100 of the actuator system 101. In this regard, diaphragm 124 is acted upon by reciprocating operating shaft 150, which is interconnected with diaphragm 124 at extremity 150a thereof. At its other extremity 150b, operating shaft 150 is acted upon by shaft 95a of motor 95 as the motor shaft reciprocates under the control of the motion controller 98.

As the operating shaft 150 of the actuating system reciprocates, diaphragm 124 acts upon a pressure transmissive fluid contained within the actuator chamber in a manner to generate a pulsatile pressure on the transmissive fluid. The pulsatile pressure generated on the transmissive fluid in turn results in a pulsatile pressure being exerted on bladder 114 in a manner to controllably vary the volume thereof. As the bladder 114 is collapsed by the pressure exerted on the bladder by the pressure transmissive fluid, blood is forced outwardly of the delivery port 120 of the bladder and through the novel tricuspid valve 156 that is mounted within the delivery port (FIG. 19). Conversely, a reduction in pressure of the transmissive fluid caused by a retraction of the reciprocating shaft 150 permits the compressible-expandable bladder 114 to expand in a manner to allow highly desirable positive pressure/passive infilling via the inflow or receiving port 118 via the tricuspid valve 154 that is mounted within the port (see FIG. 19).

As in the earlier described embodiments, tricuspid valves 154 and 156 which are held in position by threaded connectors 157 uniquely mimic the shape and action of the native tricuspid heart valve which is located on the right side of the heart between the right atrium and the right ventricle. During normal operation of the heart, the right atrium receives deoxygenated blood from the superior and inferior vena cavae and the coronary sinus and pumps it into the right ventricle through the heart's tricuspid valve. As indicated in FIG. 19, both of the tricuspid valves 154 and 156 as well as both of the threaded connectors 157, are coated with proprietary coating "C".

Continued operation of the pulsatile flow pump 108, the hydraulic actuating sub-assembly 100, and motor system 95 which is under the control of the controller system 98, may generate a physiologic pulsatile blood flow that very accurately duplicates blood pressure and flow patterns of the patient while handling the patient's blood gently.

As previously mentioned, when the apparatus is used to partially support a beating heart in carrying out procedures such as ventricular assist and Extracorporeal Membrane Oxygenation (ECMO), a certain timing of each beat of the pump is beneficial. In this regard, medical research has shown that a pump system that is assisting a beating heart may beneficially trigger shortly after the actual heart beat. Pumping at the same time actually puts an additional load on the heart. The variable delay allows the exact desired time interval to be set which gives optimal healing. Each beat shows two pressure peaks on the monitor.

Turning now to FIG. 21 of the drawings, still another embodiment is there illustrated and generally designated by the numeral 160. This apparatus is similar in most respects to the apparatus described in the preceding paragraphs and designated in the drawings by the numeral 90. As indicated in FIG. 21, the apparatus of this latest embodiment comprises first and second substantially identical pulsatile flow pumps 108a and 108b that are interconnected via a "Y" connector 162 with actuator system 101 that is substantially identical in construction and operation to that previously described. Pulsatile flow pumps 108a and 108b have a volume of between about 1 ml and about 100 ml.

In operating this latest embodiment, the actuator system 101, which includes the hydraulic actuating sub-assembly 100, simultaneously actuates pulsatile flow pumps 108a and 108b in the same manner as a healthy heart. This novel two-chamber pumping system provides physiologic flows and pressures to both the systemic and pulmonary circulations, even though the pressure in the lungs is about ⅕ of the systemic circulation. Uniquely, this novel two-chamber pumping system greatly affects mortality and morbidity patient outcomes.

Figure 22:
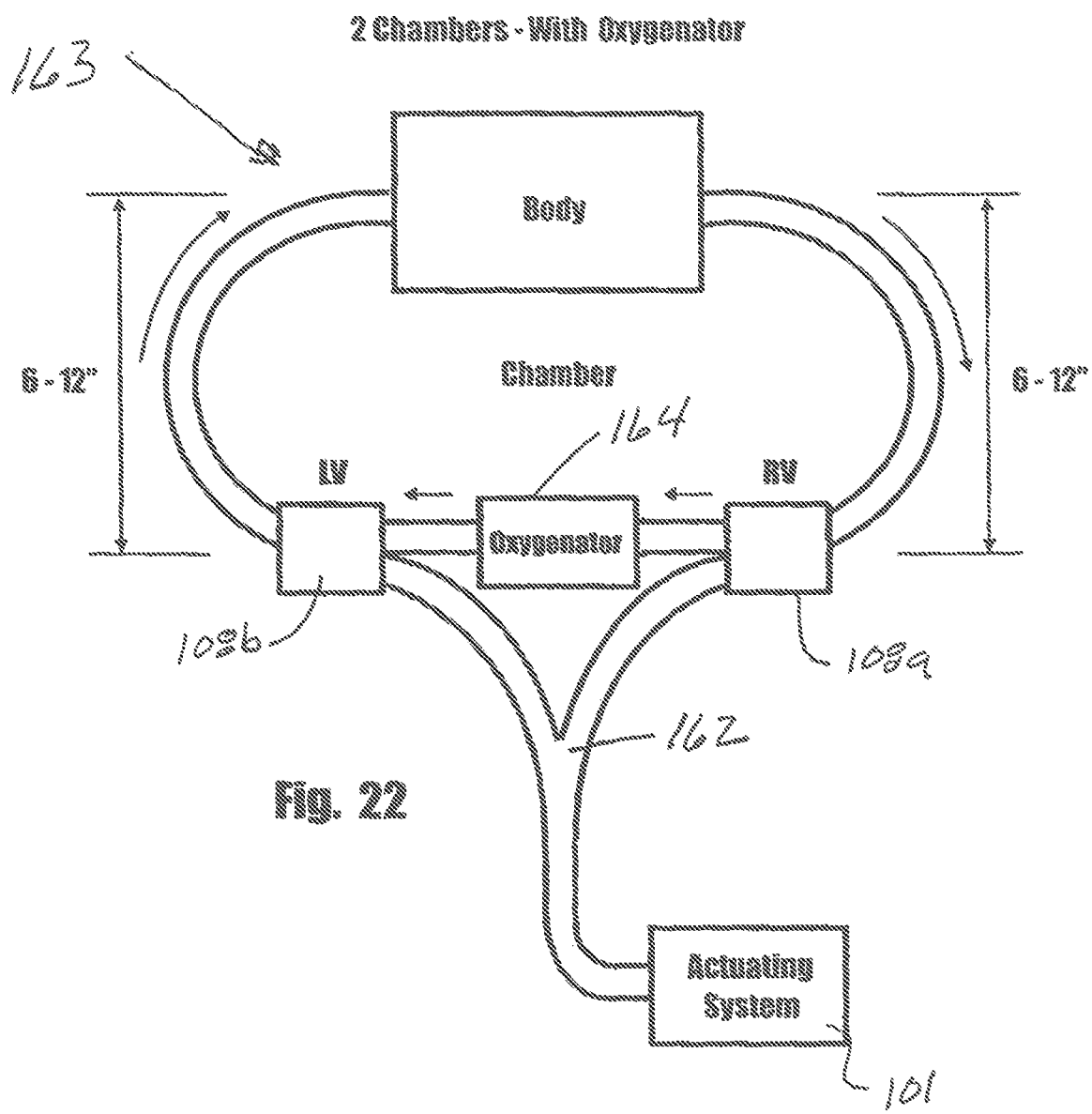
FIG. 22 is a generally diagrammatic view illustrating the manner of interconnection of the hydraulic actuator sub-assembly and a further embodiment of the pulsatile pump sub-assembly with the patient.

Referring finally to FIG. 22 of the drawings, yet another embodiment is there illustrated and generally designated by the numeral 163. This apparatus is similar in most respects to the previously described apparatus 160 and like numerals are used in FIG. 22 to identify like components. As indicated in FIG. 22, the apparatus of this latest embodiment also comprises first and second substantially identical pulsatile flow pumps 108a and 108b, each having a volume of between about 1 ml and about 100 ml. Pulsatile flow pumps 108a and 108b are interconnected with actuator system 101 via a "Y" connector 162 to provide a system that is substantially identical in construction and operation to that previously described. However, in the manner shown in FIG. 22, in this latest embodiment a known oxygenator 164 is disposed between and interconnected with the first and second pulsatile flow pumps 108a and 108b. Accordingly, pump 108a functions as a pre-oxygenator and pump 108b functions as a post-oxygenator. While oxygenator 164 is commercially available from various sources, an oxygenator offered for sale by the Dideco Company of Arvada, Colo. has proven satisfactory for use in the apparatus of FIG. 22.

As was the case in operating the embodiment shown in FIG. 21 of the drawings, the actuator system 101, which includes the hydraulic actuating sub-assembly 100, simultaneously actuates pulsatile flow pumps 108a and 108b in the same manner as a healthy heart and the oxygenator functions to exchange oxygen and carbon dioxide in the blood of the patient during the surgical procedure.

FIG. 20 depicts a system employing one chamber and may be suitable for cord blood stem cell collection and for left or right ventricular assist. That is, the circuit diagram may be of an assist to either the systemic circulation (LVAD) or pulmonary circulation (RVAD). The patient's lungs would oxygenate the blood. In LVAD, inflow is from pulmonary vein, outflow to aorta. In RVAD, inflow is from vena cava (venous return to heart), outflow to pulmonary arteries.

A cord blood stem cell harvesting circuit uses a single chamber, as do the LV or RV assist circuits. However it is different from either of them, in that the other two are closed circuits, but the cord blood stem cell harvesting circuit is a one-way trip. The circuit does not repeat because a tube from a reservoir is connected to the inflow side of the chamber. The outflow side has two branches via the use of a Y-connector. A cannula is placed on each branch and each of the two cannulas is inserted respectfully into the two umbilical arteries. A perfusion solution is pumped through the cord and placenta and collected at the outflow of the umbilical vein. This is a one-way flow, and not a continuous circulation as in an "assist."

FIG. 21 depicts a system employing two chambers and no oxygenator, creating accurate systemic and pulmonary pulse pressures used for biventricular assist.

FIG. 22 depicts a system employing two chambers with an oxygenator and may be used for regional cancer therapy, organ preservation, cardiopulmonary bypass, ECMO, etc. One chamber is post-oxygenator, so there is no dampening of physiologic blood pressure and flow patterns as often caused by an oxygenator.

Accurate physiologic hemodynamic emulation of natural circulatory blood pressure and flow patterns employed in the embodiments has proved vastly superior to non-pulsatile flow and to mere non-physiologic "pulsatile flow." Accurate physiologic hemodynamic emulation of natural circulatory blood pressure and flow patterns decreases incidence of post-operative deaths in pediatric and adult patients, significantly increases blood flow of vital organs including brain, heart, liver, and pancreas, reduces systemic inflammatory response syndrome, significantly increases vital organ recovery in several types of animal models when compared to non-physiologic "pulsatile" perfusion, and generates more hemodynamic energy, which better maintains the microcirculation compared with non-physiologic "pulsatile" flow.

The methods described employ an apparatus that can accurately duplicate a blood pressure curve by independently varying pulse rate, that is the number of beats per minute; stroke volume, that is the volume of blood pumped on each beat; and upstroke-rise time, that is the duration of time from the start to peak pressure at the top of the curve on each beat. In a potential clinical application, for example, a cardiopulmonary bypass procedure or an organ preservation procedure, this duplication of the blood pressure curve can be achieved by methods that include the following steps.

The first step in the process is to obtain in a known manner, a blood pressure chart recorder tracing from the patient or organ being treated. Using this charted information as a guide, once the pulse wave and flow patterns are duplicated by independent control of a plurality of circulatory impulsion variables, pressure and flow may be controlled by the peripheral resistance of the blood vessels. There may be no significant variance in blood pressure/flow patterns, the capillary beds (microcirculation) may be filled and flushed with a full flow of blood; there may be normal oxygenation of all tissues; and all waste products (metabolites) may be effectively removed.

Duplication of the pulse wave and flow patterns may be accomplished with sufficient exactitude to produce accurate systolic and diastolic patterns of the given patient, adjusting these profiles as needed. These relate as follows:

Systolic Blood Pressure: The maximum arterial pressure in mm Hg, for any given blood vessel during the ejection phase of the pump cycle;

Diastolic Blood Pressure: The minimum arterial pressure in mm Hg, for any given blood vessel during the "relaxation" phase of the pump cycle; and Pulse Pressure: The difference between systolic and diastolic pressure in mm Hg.

Diastolic pressures are often about ⅔ of systolic pressure; however, these values can vary considerably among individuals, e.g., a blood pressure reading of 120/80: Systolic pressure=120 mm Hg; Diastolic pressure=80 mm Hg.

The pumping or perfusion is commenced by pre-setting pulse rate and upstroke rise time parameters obtained from a chart recorder, and then manipulating the stroke volume in such a manner that the blood pressure curve matches the chart recorder blood pressure reading previously obtained for the subject patient. Other applications such as ventricular assist (LVAD, RVAD, BiVAD), ECMO, etc., may have different perfusion parameters, and the embodiments are uniquely able to adapt to each application.

When the herein taught method is used to partially support a beating heart in carrying out procedures such as ventricular assist and extracorporeal membrane oxygenation (ECMO), a certain timing of each beat of the pump is beneficial. In this regard, research has shown that a pump system that is assisting a beating heart may beneficially trigger shortly after the actual heart beat. Pumping at the same time actually puts an additional load on the heart. The variable delay allows the exact desired time interval to be set which gives optimal healing. Each beat shows two pressure peaks on the monitor.

In accomplishing the procedures identified in the preceding paragraph, the apparatus supporting the method uniquely includes an EKG trigger circuit. So configured, the system can be triggered by an electronic EKG signal obtained from the patient's heart so that it "beats" every time the patient's heart beats. In some laboratory studies, when a heart was removed and placed on an oxygen preservation perfusion machine, the heart continued to beat out of the body (ex vivo). In such a situation, preservation methods employing accurate physiologic hemodynamic emulation of natural circulatory blood pressure and flow patterns may use an EKG-trigger with a variable delay. In this configuration, when the EKG-trigger is activated, the trigger uniquely overrides the usual pulse rate control.

A method of employing accurate physiologic hemodynamic emulation of natural circulatory blood pressure and flow patterns to extract stem cells from a non-embryonic stem cell source includes using a non-embryonic stem cell source comprising stem cells and perfusing the non-embryonic stem cell source with a perfusion solution by establishing a perfusion circuit introducing the perfusion solution into the non-embryonic stem cell source, thereby producing perfusate containing stem cells. The method may include isolating the stem cells from the perfusate. The hemodynamic emulation may be accomplished in the various embodiments described herein by accurate duplication of blood pressure and flow patterns as is capable of being represented on a chart recorder or monitor, the duplication accomplished by judicious independent adjustment of pulse-rate, stroke volume, and upstroke rise time.

By way of example, the hemodynamic emulation may be accomplished by incorporating a man-made device into the perfusion circuit. The method may further include priming the device and perfusion circuit with a priming solution prior to introducing perfusion solution into the perfusion circuit. The non-embryonic stem cell source may include one or more members selected from the group consisting of a human or animal placenta and a human or animal umbilical cord. The priming solution may include perfusion solution.

The method may further include, prior to perfusing the stem cell source, administering an anticoagulant to the non-embryonic stem cell source. The anticoagulant may include one or more members selected from the group consisting of heparin and warfarin sodium. Perfusing may be carried out under conditions that simulate conditions of the non-embryonic stem cell source in vivo. Introduction of perfusion solution under may be accomplished at one or more systolic pressures between 20 mm Hg to 150 mm Hg, inclusive, and at one or more perfusion solution temperatures between 4 degrees C. to 40 degrees C., inclusive. Introduction of perfusion solution under the hemodynamic emulation may be accomplished at one or more systolic pressures between 60 mm Hg to 120 mm Hg, inclusive, and at one or more perfusion solution temperatures between 15 degrees C. to 20 degrees C., inclusive. The perfusion solution may include cell culture media.

The perfusion solution may include one or more members selected from the group consisting of BES, BIS-TRIS, BIS-TRIS propane, EPPS, Gly-Gly, HEPES, HEPES sodium salts, MES hydrate, MES sodium salts, MOPS, MOPS sodium salts, PIPES, TAPS, TAPS sodium salts, TAPSO TES, Tricine, Trizma® base, Trizma® Hydrochloride, Trizma® hydrochloride buffer solution, Trizma® Preset crystals, Alsever's Solution, Ames Medium, Basal Medium Eagle, Click's Medium, Dulbecco's Modified Eagle's Medium-high glucose, Dulbecco's Modified Eagle's Medium-low glucose, Dulbecco's Modified Eagle's Medium/Nutrient Mixture F-12 Ham, Dulbecco's Phosphate Buffered Saline, Earle's Balanced Salts, Gey's Balanced Salt Solution, Glasgow Minimum Essential Medium, Grace's Insect Medium, Hanks' Balanced Salt Solution, IPL-41 Insect Medium, Iscove's Modified Dulbecco's Medium, Iscove Modified Dulbecco's Medium, Krebs-Henseleit Buffer Modified, Krebs-Ringer bicarbonate buffer, L-15 Medium (Leibovitz), McCoy's 5A Medium, MCDB 105 Medium, MCDB 110 Medium, MCDB 131 Medium, MCDB 153 Medium, MCDB 201 Medium, Medium 199, Mega Cell™ Dulbecco's Modified Eagle's Medium, Mega Cell™ Dulbecco's Modified Eagles Medium/Nutrient Mixture F-12 Ham, Mega Cell™ Minimum Essential Medium Eagle, Mega Cell™ Minimum Essential Medium/Nutrient Mixture F-12 Ham, Mega Cell™ RPMI-1640 Medium, Minimum Essential Medium Eagle, NCTC 109 Medium, Nutrient Mixture F-10 Ham, Nutrient Mixture F-12 Ham, RPMI 1640, RPMI 1640 Medium with L-glutamine and sodium bicarbonate, RPMI 1640 HEPES Modification with 25 mM HEPES without L-glutamine, RPMI 1640 medium Modified with 20 mM HEPES and L-glutamine and sodium bicarbonate, RPMI 1640 Medium with sodium bicarbonate without L-glutamine, RPMI 1640 Medium Dutch Modification with sodium bicarbonate and 20 mM HEPES without L-glutamine, RPMI 1640 medium 10X without glutamine, folic acid and sodium bicarbonate, RPMI 1640 medium modified with sodium bicarbonate without methione, cystine and L-glutamine, RPMI 1640 medium modified with sodium bicarbonate without L-glutamine and phenol red, RPMI 1640 medium HEPES modification, with L-glutamine 25 mM HEPES without sodium bicarbonate, RPMI 1640 medium with L-glutamine without glucose and sodium bicarbonate, RPMI 1640 medium modified with L-glutamine without phenol red and sodium bicarbonate, RPMI 1640 medium powder, AutoMod™ cell cultured tested, Schneider's insect medium, Shields and Sang M3 insect medium, Shields and Sang M3 insect medium, TC-100 insect medium, TNM-FH insect medium, Tyrode's salts, Waymouth MB 752/1 medium, Williams' medium E, Hanks, Eagles, Albumin, Beizer Machine perfusion solution, Celsior, Euro-Collins, Vitrolife Perfadex solution, Vitrolife Steen solution, Custodial HTK solution, PSI Mapersol solution, Lifeblood Medical Lifor solution, Sterile Saline HTK, Lactated Ringers, Plasmanate, Hespan, Normal Saline, IGL, Vasosol, and Viaspan.

The perfusion solution may include one or more members selected from the group consisting of a colloidal agent, an anti-edema agent, an antioxidant, an anti-inflammatory agent, a vasodilator, an antimicrobial agent, and a combination of any two or more thereof. Accordingly, the perfusion solution may include a colloidal agent, an anti-edema agent, an antioxidant, an anti-inflammatory agent, and a vasodilator. The perfusion solution may have a pH, temperature corrected to 37° C., within a range of 7.35 to 7.45, and an osmolality in the range of 300 to 400 mOsmols. The osmolality may be in the range of 310 to about 350 mOsmols.

The isolating may include subjecting the perfusate containing stem cells to one or more of density gradient centrifugation, magnet cell separation, affinity cell separation, flow cytometry, and cell sorting, to produce isolated stem cells. The method may further include cryopreserving the isolated stem cells.

A method for producing a non-embryonic stem cell line includes using a non-embryonic stem cell source containing stem cells. The method includes perfusing the non-embryonic stem cell source with a perfusion solution by establishing a perfusion circuit introducing accurate physiologic hemodynamic emulation of natural circulatory blood pressure and flow patterns of the perfusion solution into the non-embryonic stem cell source, thereby producing perfusate comprising stem cells. The stem cells may be isolated from the perfusate. The method includes culturing the isolated stem cells in stem cell culture media to produce the non-embryonic stem cell line.

A method for producing a vascularized tissue or organ for grafting or implantation includes employing accurate physiologic hemodynamic emulation of natural circulatory blood pressure and flow patterns to extract stem cells from a non-embryonic stem cell by the methods above. The present method includes isolating arteries from a "decellularised" tissue or organ graft, and perfusing the graft with a stem cell solution.

A method of employing accurate physiologic hemodynamic emulation of natural circulatory blood pressure and flow patterns to preserve biological organs includes perfusing an ex vivo organ, by introduction to the organ, via a perfusion circuit, of a perfusion solution having a perfusate containing an oxygenated non-blood solution. The introduction accomplished via the hemodynamic emulation. The biological organ preservation method may be performed under normothermic or hypothermic conditions. The perfusate may further contain a blood solution. The method may include priming the device and perfusion circuit with a priming solution prior to introducing perfusion solution into the perfusion circuit.

A method of providing systemic circulation, to perform heart-functions for a living subject that is undergoing a surgical procedure, includes providing circulatory impelling energy that emulates accurate physiologic hemodynamic emulation of natural circulatory blood pressure and flow patterns. The method includes perfusing the patient's systemic circulation system with a perfusion solution via a perfusion circuit. The perfusion circuit includes a perfusate containing oxygenated blood and priming solution. The perfusing occurs via the hemodynamic emulation. The methods according to the various embodiments described herein may include reducing the perfusion circuit priming volume compared to known priming volumes often used, thereby, reducing hemodilution.

The hemodynamic emulating impelling energy may be achieved by incorporating a man-made device into the patient's systemic circulation system. The method may further include priming the perfusion circuit with a priming solution prior to introducing the perfusion solution into the patient's systemic circulation.

A method employing accurate physiologic hemodynamic emulation of natural circulatory blood pressure and flow patterns to provide ventricular assistance includes perfusing systemic and, alternatively or concurrently, pulmonary circulatory systems via a perfusion circuit with perfusion solution having a perfusate containing blood and priming solution. The process of the perfusion is synchronized with a patient's beating heart, wherein the perfusion is accomplished by accurate duplication of blood flow as is capable of being represented on a blood pressure curve chart.

The emulation may employ an EKG trigger circuit having variable trigger response delay capability. The EKG trigger circuit may include a sensor that detects the patient's heartbeat and, alternatively or concurrently, detects the patient's hemodynamic patterns. The EKG trigger circuit, under or by judicious control of the variable trigger response delay capability, regulates delivery of the perfusate, such that it is synchronized with the patient's heartbeat. Delivery of perfusate may be synchronized with the patient's beating heart via an EKG-trigger circuit with a variable trigger response delay. The method may include reducing the perfusion circuit priming volume, thereby reducing hemodilution. The hemodynamic emulation may be accomplished by incorporating a man-made device into the perfusion circuit.

A method of performing ECMO (extra corporeal membrane oxygenation) includes perfusing a patent's systemic circulation with a perfusion solution, via an ECMO circuit having a perfusate containing oxygenated blood and priming solution. The perfusion is accomplished via delivery of perfusate to the ECMO circuit. The delivery may be synchronized with a patient's beating heart by accurate physiologic hemodynamic emulation of natural circulatory blood pressure and flow patterns accomplished by accurate duplication of blood pressure and flow patterns as is capable of being represented on a chart recorder or monitor. The emulation may employ an EKG-trigger circuit having variable trigger response delay capability, as described herein.

The hemodynamic emulation may be accomplished by incorporating a man-made device into the patient's systemic circulation system. The method may further include priming the ECMO circuit with a priming solution prior to introducing the perfusion solution into the patient's systemic circulation. Performing the ECMO may include performing neonatal ECMO.

A method of employing accurate physiologic hemodynamic emulation of natural circulatory blood pressure and flow patterns for regional cancer therapy includes perfusing in vivo isolated organs or body regions with accurate physiologic hemodynamic emulation of natural circulatory blood pressure and flow patterns via a perfusion circuit. A perfusion solution is employed with a perfusate containing an oxygenated anti-cancer non-blood and blood solution, wherein the hemodynamic emulation is accomplished by accurate duplication of blood pressure and flow patterns flow as is capable of being represented on a chart recorder or monitor. The method includes delivering the perfusate while the patient is under normothermic or hypothermic conditions. The method may be accomplished by incorporating a man-made device into the perfusion circuit.

A method of accurate physiologic hemodynamic emulation of natural circulatory blood pressure and flow patterns to perform stem cell delivery includes perfusing in vivo isolated organs or body regions via a perfusion circuit with accurate physiologic hemodynamic emulation of natural circulatory blood pressure and flow patterns. The perfusing employs a perfusion solution with a perfusate containing an oxygenated stem cell and blood solution. The hemodynamic emulation is accomplished by accurate duplication of blood pressure and flow patterns flow as is capable of being represented on a chart recorder or monitor.

The method may include reducing perfusion circuit priming volume, to reduce hemodilution. The hemodynamic emulation may be accomplished by incorporating a man-made device into the perfusion circuit. The method may include priming the device and perfusion circuit with a priming solution prior to introducing perfusion solution into the perfusion circuit.

By way of example, the methods described herein may be performed for neonates/infants, according to the needs of the individual patient. Therein, pulse rate may be set between 100 beats/minute and 200 beats/minute. Upstroke rise time may be set between 0.06 second and 0.2 second (60 milliseconds and 200 milliseconds). Stroke volume (volume for each beat) may be set between 1 ml and 10 ml. Flow (volume/minute) may be set between 0.1 liter and 1 liter/minute.

Also, the methods described herein may be performed for small children/adolescents, according to the needs of the individual patient. Therein, pulse rate may be set between 60 beats/minute and to 120 beats/minute. Upstroke rise time may be set between 0.1 second to 0.3 second (100 milliseconds and 300 milliseconds). Stroke volume may be set between 10 ml and 80 ml. Flow may be set between 1 liter and 6 liters/minute.

Further, the methods described herein may be performed for adults, according to the needs of the individual patient. Pulse rate may be set between 30 beats/minute and to 100 beats/minute. Upstroke rise time may be set between 0.1 second and 0.6 second (100 milliseconds and 600 milliseconds). Stroke volume may be set between 30 ml and 120 ml. Flow may be set between 3 liters/minute and 12 liters/minute.

As appreciated from the description herein, an extracorporeal pumping method includes receiving an inlet fluid into a compressible-expandable bladder sealably mounted within a housing and moving an actuating member mounted within a fluid chamber of a hydraulic actuating sub-assembly. The fluid chamber contains a pressure transmissive fluid. Transmissive fluid is displaced from the fluid chamber into the housing. The method includes compressing a volume of the bladder in the housing the transmissive fluid displaced into the housing, the compressed bladder ejecting the inlet fluid from the bladder to provide an outlet fluid under pulsatile pressure. The actuating member is moved within the fluid chamber and the displaced transmissive fluid is returned from the housing into the fluid chamber. The method includes expanding the compressed bladder in the housing and receiving additional inlet fluid into the bladder. The movement of the actuating member is controlled such that the outlet fluid exhibits a predetermined pulse rate, stroke volume, and upstroke rise time.

By way of example, the pumping method may be a blood pumping method. The outlet fluid may be introduced into a blood vessel and thereby pump blood through the blood vessel under the pulsatile pressure. The motion controller may control pulse rate, stroke volume, and upstroke rise time independently. The method may further include programming the predetermined pulse rate, stroke volume, or upstroke rise time into the motion controller using a programmable touch screen. Also, the method may further include programming the predetermined pulse rate into the motion controller using an EKG trigger. The inlet fluid may be received into the bladder through a first valve, which may be a tricuspid valve. The outlet fluid may be ejected from the bladder through a second valve, which may be a tricuspid valve too.

The inlet fluid may contain a perfusion solution. Accordingly, the method may further include extracting umbilical cord blood and/or placenta stem cells using the outlet fluid. Also, the method may further include providing stem cell therapy using the outlet fluid. The inlet fluid may contain blood. Accordingly, the method may further include providing cardiopulmonary bypass, ventricular assist, extracorporeal membrane oxygenation, organ preservation, fetal cardiac bypass, or cancer treatment using the outlet fluid.

The method may further include preparing the hydraulic actuating sub-assembly for use in the blood pumping method by introducing the pressure transmissive fluid into the fluid chamber through a fill port in an operating shaft, the operating shaft being interconnected and reciprocally moveable with the actuating member. Additionally, the method may further include monitoring the position and velocity of a shaft in a communicating motor system, the shaft acting on the actuating member to generate the movement of the actuating member.

As will be further appreciated, an extracorporeal pumping method includes receiving an inlet fluid through a first tricuspid valve into a compressible-expandable bladder sealably mounted within a housing and moving an actuating member mounted within a fluid chamber of a hydraulic actuating sub-assembly. The fluid chamber contains a pressure transmissive fluid and the method includes displacing transmissive fluid from the fluid chamber into the housing. A volume of the bladder is compressed in the housing the transmissive fluid displaced into the housing, the compressed bladder ejecting the inlet fluid from the bladder through a second tricuspid valve to provide an outlet fluid under pulsatile pressure. The method includes moving the actuating member within the fluid chamber, returning the displaced transmissive fluid from the housing into the fluid chamber, expanding the compressed bladder in the housing, and receiving additional inlet fluid into the bladder.

A predetermined pulse rate, stroke volume, and upstroke rise time are programmed into a motion controller, the motion controller controlling pulse rate, stroke volume, and upstroke rise time independently. The movement of the actuating member is controlled using the motion controller such that the outlet fluid exhibits the predetermined pulse rate, stroke volume, and upstroke rise time. The method includes monitoring the position and velocity of a shaft in a communicating motor system, the shaft acting on the actuating member to generate the movement of the actuating member.

These and other methods described herein may be used to provide the outlet fluid under the pulsatile pressure to extract umbilical cord blood and/or placenta stem cells or to provide stem cell therapy, cardiopulmonary bypass, ventricular assist, extracorporeal membrane oxygenation, organ preservation, fetal cardiac bypass, or cancer treatment.

In compliance with the statute, the embodiments have been described in language more or less specific as to structural and methodical features. It is to be understood, however, that the embodiments are not limited to the specific features shown and described. The embodiments are, therefore, claimed in any of their forms or modifications within the proper scope of the appended claims appropriately interpreted in accordance with the doctrine of equivalents.

The invention claimed is:

1. An extracorporeal pumping method comprising:
   receiving an inlet fluid into a compressible-expandable bladder sealably mounted within a housing;
   moving an actuating member mounted within a fluid chamber of a hydraulic actuating sub-assembly, the fluid chamber containing a pressure transmissive fluid, and displacing transmissive fluid from the fluid chamber into the housing;
   compressing a volume of the bladder in the housing the transmissive fluid displaced into the housing, the compressed bladder ejecting the inlet fluid from the bladder to provide an outlet fluid under pulsatile pressure;
   introducing the outlet fluid into a blood vessel and thereby pumping blood through the blood vessel under the pulsatile pressure;
   moving the actuating member within the fluid chamber and returning the displaced transmissive fluid from the housing into the fluid chamber;
   expanding the compressed bladder in the housing and receiving additional inlet fluid into the bladder; and
   controlling the movement of the actuating member such that the outlet fluid exhibits a predetermined pulse rate, stroke volume, and upstroke rise time.

2. The method of claim 1 wherein the movement of the actuating member is controlled using a programmable motion controller.

3. The method of claim 2 wherein the motion controller controls pulse rate, stroke volume, and upstroke rise time independently.

4. The method of claim 3 further comprising programming the predetermined pulse rate, stroke volume, or upstroke rise time into the motion controller using a programmable touch screen.

5. The method of claim 3 further comprising programming the predetermined pulse rate into the motion controller using an EKG trigger.

6. The method of claim 1 wherein the inlet fluid is received into the bladder through a first valve.

7. The method of claim 6 wherein the first valve is a tricuspid valve.

8. The method of claim 1 wherein the outlet fluid is ejected from the bladder through a second valve.

9. The method of claim 8 wherein the second valve is a tricuspid valve.

10. The method of claim 1 wherein the inlet fluid comprises a perfusion solution.

11. The method of claim 1 further comprising extracting umbilical cord blood and/or placenta stem cells using the outlet fluid.

12. The method of claim 1 further comprising providing stem cell therapy using the outlet fluid.

13. The method of claim 1 wherein the inlet fluid comprises blood.

14. The method of claim 1 further comprising providing cardiopulmonary bypass, ventricular assist, extracorporeal membrane oxygenation, organ preservation, fetal cardiac bypass, or cancer treatment using the outlet fluid.

15. The method of claim 1 further comprising preparing the hydraulic actuating sub-assembly for use in the blood pumping method by introducing the pressure transmissive fluid into the fluid chamber through a fill port in an operating shaft, the operating shaft being interconnected and reciprocally moveable with the actuating member.

16. The method of claim 1 further comprising monitoring the position and velocity of a shaft in a communicating motor system, the shaft acting on the actuating member to generate the movement of the actuating member.

17. An extracorporeal pumping method comprising:

receiving an inlet fluid through a first tricuspid valve into a compressible-expandable bladder sealably mounted within a housing;

moving an actuating member mounted within a fluid chamber of a hydraulic actuating sub-assembly, the fluid chamber containing a pressure transmissive fluid, and displacing transmissive fluid from the fluid chamber into the housing;

compressing a volume of the bladder in the housing the transmissive fluid displaced into the housing, the compressed bladder ejecting the inlet fluid from the bladder through a second tricuspid valve to provide an outlet fluid under pulsatile pressure;

moving the actuating member within the fluid chamber and returning the displaced transmissive fluid from the housing into the fluid chamber;

expanding the compressed bladder in the housing and receiving additional inlet fluid into the bladder;

programming a predetermined pulse rate, stroke volume, and upstroke rise time into a motion controller, the motion controller controlling pulse rate, stroke volume, and upstroke rise time independently;

controlling the movement of the actuating member using the motion controller such that the outlet fluid exhibits the predetermined pulse rate, stroke volume, and upstroke rise time;

monitoring the position and velocity of a shaft in a communicating motor system, the shaft acting on the actuating member to generate the movement of the actuating member; and using the outlet fluid under the pulsatile pressure to extract umbilical cord blood and/or placenta stem cells or to provide stem cell therapy, cardiopulmonary bypass, ventricular assist, extracorporeal membrane oxygenation, organ preservation, fetal cardiac bypass, or cancer treatment.

18. The method of claim 17 further comprising programming the predetermined pulse rate, stroke volume, and upstroke rise time into the motion controller using a programmable touch screen.

19. The method of claim 17 further comprising programming the predetermined pulse rate into the motion controller using an EKG trigger.

20. The method of claim 17 wherein using the outlet fluid under the pulsatile pressure comprises extracting umbilical cord blood and/or placenta stem cells.

\* \* \* \* \*